United States Patent [19]
Yang et al.

[11] Patent Number: 6,159,731
[45] Date of Patent: Dec. 12, 2000

[54] DAXX, A FAS-BINDING PROTEIN THAT ACTIVATES JNK AND APOPTOSIS

[75] Inventors: Xiaolu Yang, Philadelphia, Pa.; Roya Khosravi-Far, Malden; Howard Y. Chang, Cambridge, both of Mass.; David Baltimore, Pasadena, Calif.

[73] Assignee: Massachusetts Institute of Technology, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 09/022,983

[22] Filed: Feb. 12, 1998

Related U.S. Application Data

[60] Provisional application No. 60/037,919, Feb. 12, 1997, and provisional application No. 60/051,753, Jun. 26, 1997.

[51] Int. Cl.[7] .......................... C07H 21/04; C12N 15/85; C12N 15/11; C07K 14/00
[52] U.S. Cl. ..................... 435/325; 435/69.1; 435/320.1; 435/357; 435/367; 435/369; 435/440; 530/350; 536/23.1; 536/23.5; 536/24.31; 536/24.33
[58] Field of Search .............................. 435/6, 69.1, 91.1, 435/325, 353, 357, 366, 367, 369, 320.1; 530/350; 536/23.1, 23.5, 24.31, 24.33

[56] References Cited

U.S. PATENT DOCUMENTS 5,674,734 10/1997 Leder et al. .

FOREIGN PATENT DOCUMENTS

WO 98/34946 8/1998 WIPO .

OTHER PUBLICATIONS

Nagata, *Cell* 88:355–365, 1997.
Abbas, *Cell* 84:655–658, 1996.
Rathmell et al., *Cell* 87:319–329, 1996.
Smith et al., *Cell* 76:959–962, 1994.
Itoh and Nagata, *J. Biol. Chem* . 268:10932–10937, 1993.
Tartaglia et al., *Cell* 74:845–853, 1993.
Cleveland and Ihle, *Cell* 81:479–482, 1995.
Fraser and Evan, *Cell* 85:781–784, 1996.
Chinnaiyan et al., *Cell* 81:505–512, 1995.
Boldin et al., *J. Biol. Chem* . 270:7795–7798, 1995b.
Boldin et al., *Cell* 85:803–815, 1996.
Muzio et al., *Cell* 85:817–827, 1996.
Enari et al., *Nature* 380:723–726, 1996.
Hsu et al., *Cell* 84:299–308, 1996.
Latinis and Koretzky, *Blood* 87:871–875, 1996.
Lenczowski et al., *Mol. Cell. Biol* . 17:170–181, 1997.
Goillot et al., *Proc. Natl. Acad. Sci* . USA 94:3302–3307, 1997.
Kyriakis and Avruch, *Ann. N.Y. Acad. Sci* . 766:303–319, 1996.
Verheij et al., *Nature* 380:75–79, 1996.
Xia et al., *Science* 270:1326–1331, 1995.
Smyth et al., *Transplantation* 62:1529–1532, 1996.
Via et al., *J. Immunol* . 157:5387–5393, 1996.
Baker et al., *Proc Acad. Nat'l. Sci. USA* 94:1366–1371, 1997.
Ogasawara et al., *Nature* 364:806–809, 1993.
Tanaka et al. *J. Immuno* . 158:2303–2309, 1997.
Tanaka et al., *Nature Med* . 2:317–322, 1996.
Elkon et al., *Curr. Opin. Immunol* . 8:852–859, 1996.
Adachi et al., *Nat. Genet* . 11:294–300, 1995.
Boldin et al., *J. Biol. Chem* . 270:387–391, 1995a.
Derijard et al., *Cell* 76:1025–1037, 1994.
Enari et al., *Nature* 375:78–81, 1995.
Los et al., *Nature* 375:81–83, 1995.
Tewari and Dixit., *J. Biol. Chem* . 270:3255–3260, 1995.
Itoh et al., *J. Immunol* . 151:621–627, 1993.
Lacronique et al., *Nature* 2:80–86, 1996.
Sanchez et al., *Nature* 372:794–798, 1994.
Brown et al., *Oncogene* 791–799, 1994.
Liu et al., *Cell* 87:565–576, 1996.
Gupta et al., *EMBO J* . 15:2760–2770, 1996.
Fisher et al., *Cell* 81:935–946, 1995.
Kiriakiduo et al., *DNA Cell Biol* . 16:1289–1298, 1997.
Ichijo et al., *Science* 275:90–94, 1997.
Toyoshima et al., *J. Cell. Biol* . 139:1005–1015, 1997.
Wagner, *Nature* 372:333–335, 1994.
Yang et al., *Cell* 89:1067–1076, 1997.
Chang et al., *Science* 281:1860–1863, 1998.
Hayles et al., EMBO J. 14:2760–2771, 1995.
Marra et al., GenBank accession number AA059624, Sep. 23, 1996.
Marra et al., GenBank accession number AA117247, Nov. 15, 1996.
Hillier et al., GenBank accession number W02333, Apr. 18, 1996.

*Primary Examiner*—George C. Elliott
*Assistant Examiner*—Mark L. Shibuya
*Attorney, Agent, or Firm*—Wolf, Greenfield & Sacks, P.C.

[57] ABSTRACT

The invention describes nucleic acids encoding the Daxx protein, including fragments and biologically functional variants thereof. Also included are polypeptides and fragments thereof encoded by such nucleic acids, and antibodies relating thereto. Methods and products for using such nucleic acids and polypeptides also are provided.

14 Claims, 9 Drawing Sheets

Fas CYTOPLASMIC TAIL

| DNA-BINDING HYBRID | ACTIVATION HYBRID | COLONY COLOR | β-GAL UNITS |
|---|---|---|---|
| LexA-mFasIC (165-306) | A21 | BLUE | 110 |
| LexA-mFasDD (192-295) | A21 | BLUE | 120 |
| LexA-mFasDD (192-295) | Act-DaxxC501 | BLUE | 180 |
| LexA-lpr$^{cg}$ (192-295, I224N) | A21 | LIGHT BLUE | 14 |
| LexA-mFasFD8 (192-283) | A21 | WHITE | 7 |
| LexA-hFasIC (175-319) | A21 | BLUE | 40 |
| LexA-mTNFR1DD (322-425) | A21 | BLUE | 120 |
| LexA-mCD40 IC (198-285) | A21 | WHITE | 4 |
| LexA-Bicoid | A21 | WHITE | 2 |

| ACTIVATION HYBRIDS | | | COLONY COLOR | β-GAL UNITS |
|---|---|---|---|---|
| A21 | 1 – 248 | | BLUE | 120 |
| A39 | 60 – 248 | | BLUE | 120 |
| A21N | 1 – 163 | | WHITE | 3 |
| A21C | 136 – 248 | | BLUE | 110 |
| A21C1 | 170 – 248 | | WHITE | 4 |

```
  1  MATDDSIIVLDDDDEDEAAAQPGPSNLPPNPASTGPGPGLSQQATGLSEP
 51  RVDGGSSNSGSRKCYKLDNEKLFEEFLELCKTETSDHPEVVPFLHKLQQR
101  AQSVFLASAEFCNILSRVLARSRKRPAKIYVYINELCTVLKAHSIKKKL N
151  LAPAASTTSEASGPNPPTEPPSDLTNTENTASEASRTRGSRRQIQRLEQL
201  LALYVAEIRRLQEKELDLSELDDPDSSYLQEARLKRKLIRLFGRLCELK D
251  CSSLTGRVIEQRIPYRGTRYPEVNRRIERLINKPGLDTFPDYGDVLRAV E
301  KAATRHSLGLPRQQLQLLAQDAFRDVGVRLQERRHLDLIYNFGCHLTDD Y
351  RPGVDPALSDPTLARRLRENRTLAMNRLDEVISKYAMMQDKTEEGERQK R
401  RARLLGTAPQPSDPPQASSESGEGPSGMASQECPTTSKAETDDDDDDDD D
451  DDEDDNEESEEEEEEEEEEEKEATEDEDEDLEQLQEDQGGDEEEEGGDNEGN
501  E . SPTSPSDFFHRRRNSEPAEGL . RTPEGQQKRGLTEETPASPPGASLDPPS
  1  DK -- M - SLQISNEK - L -- GKQIS - SSGE -- NK - RIVS - SLLSEEP - A - S-
549  TDAESSGEQLLEPLLGDESPVSQLAELEMEALPEE . . . . . . RDISSPRKK
 51  I - - - - N - - - PE - LT - EE - - - - - - - F - - - I - - - - LDTPSSVET - - - - S - - Q
593  SEDSLPTILENGAAVVTSTSVNGRVSSHTWRDASPPSKRFRKEKKQLGS G
101  - - EPFT - V - - - - - GM - S - - - F - - G - - P - N - G - SG - - C - KS - - - - - - T - - -
643  LLGNSYI . KEPMAQQDSGQNTSVQPMPSPPLASVASVADSSTRVDSPSHE
151  P - - - - - VERQRSVHEKN - KKICTL - S - PS - - - - L - P - - - - - - - - - - - - G
692  LVTSSLCSPSPSLLLQTPQAQSLRQCIYKTSVATQCDPEEIIVLSDSD   739
201  - - - - - - - I - - - AR - S - - - HS - PP - PGTC - - - - - - - - - - - - - - - - -   248
```

Fig. 2A

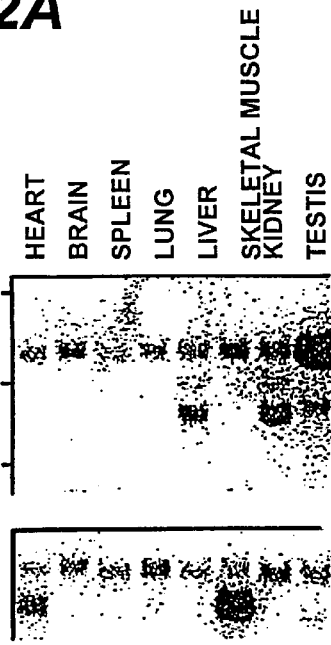

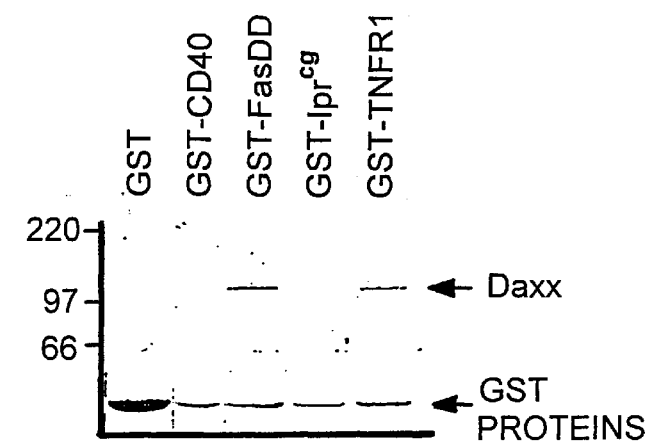
Fig. 3A
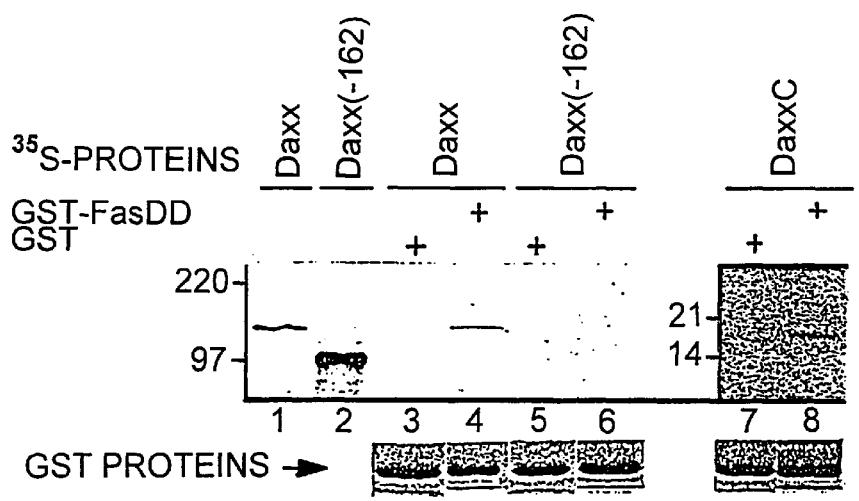
Fig. 3B
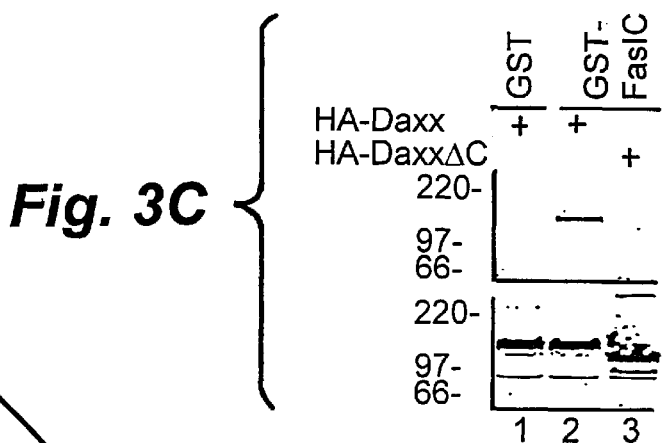
Fig. 3C
Fig. 3

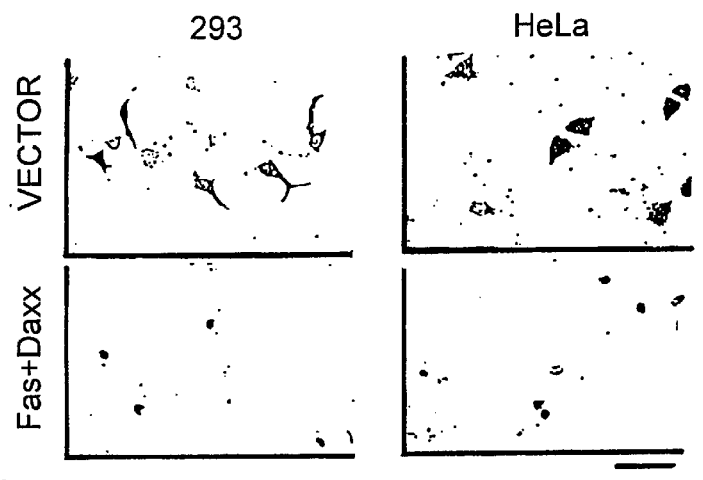
Fig. 4A
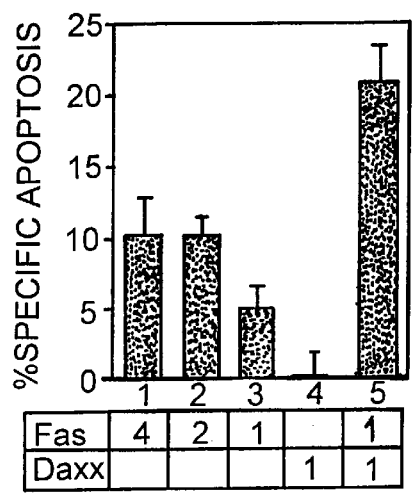
Fig. 4B
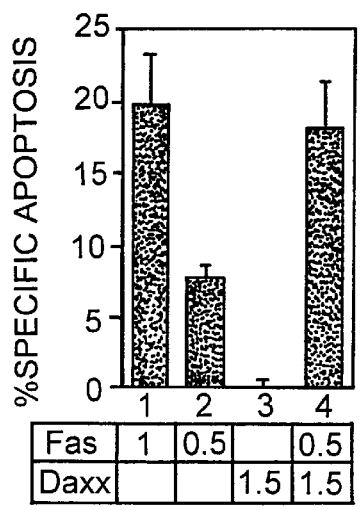
Fig. 4C
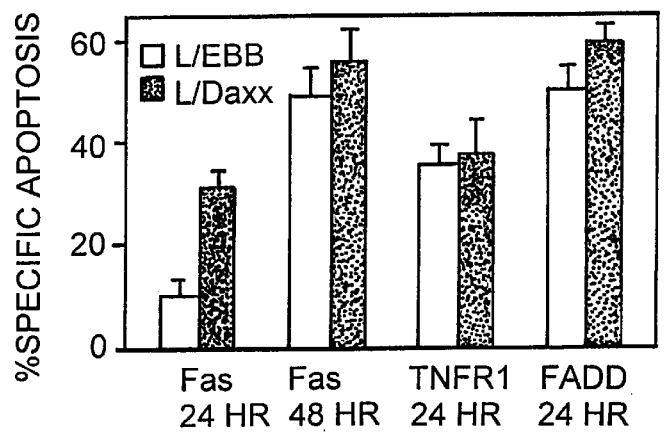
Fig. 4D
Fig. 4

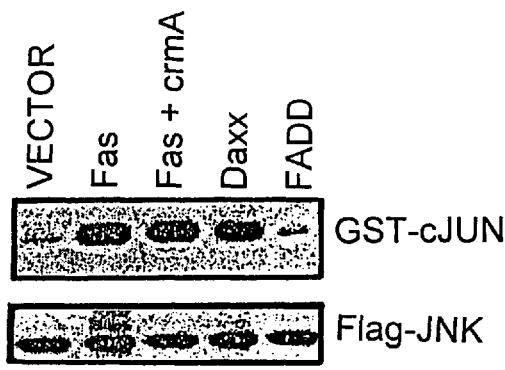
Fig. 5A
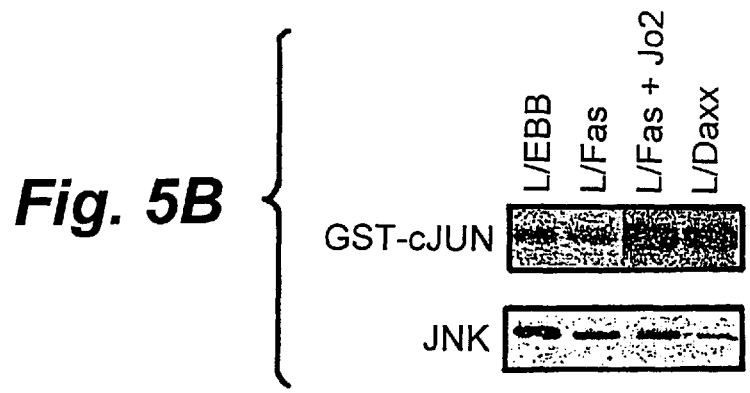
Fig. 5B
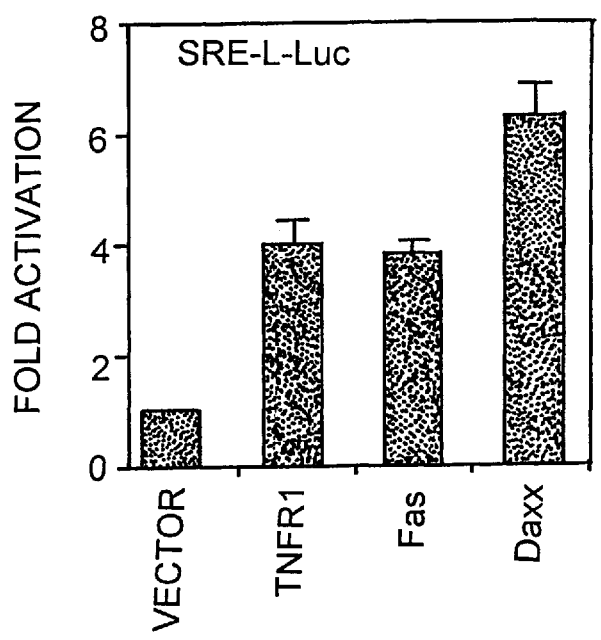
Fig. 5C
Fig. 5

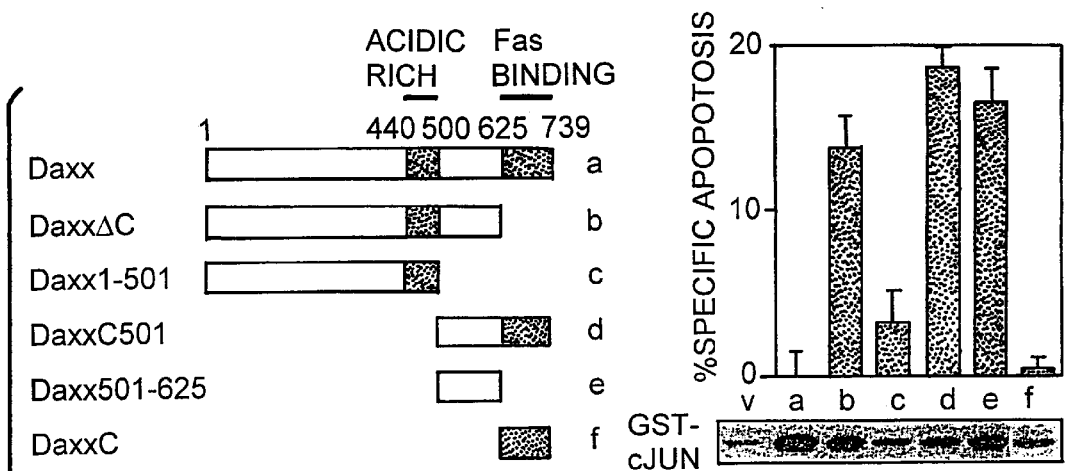
Fig. 6A
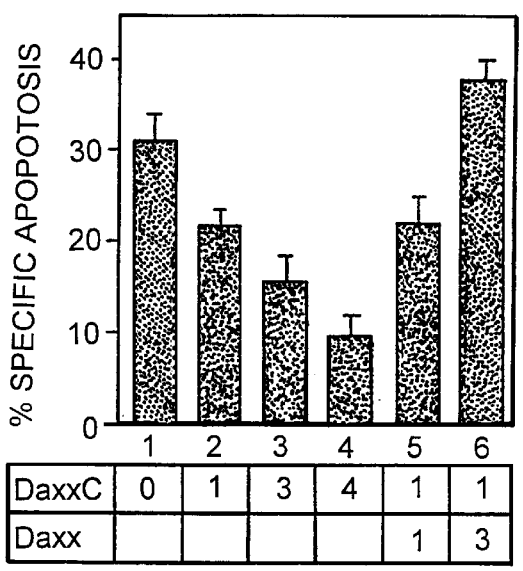
Fig. 6B
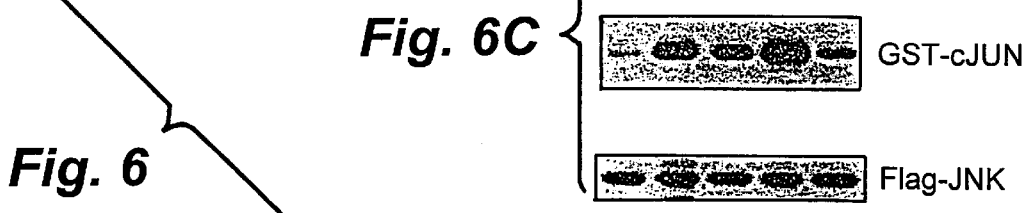
Fig. 6C
Fig. 6

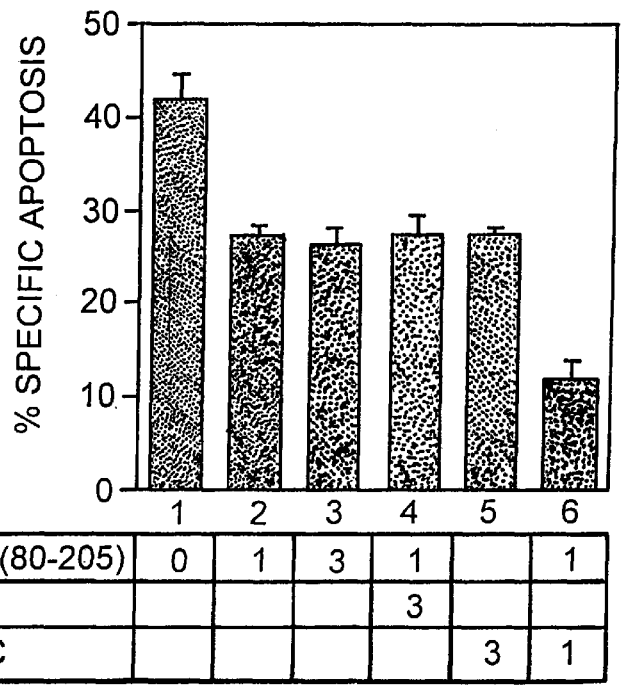
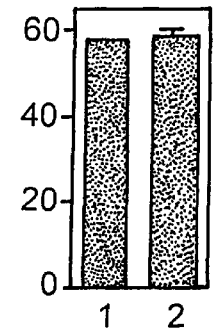
Fig. 7

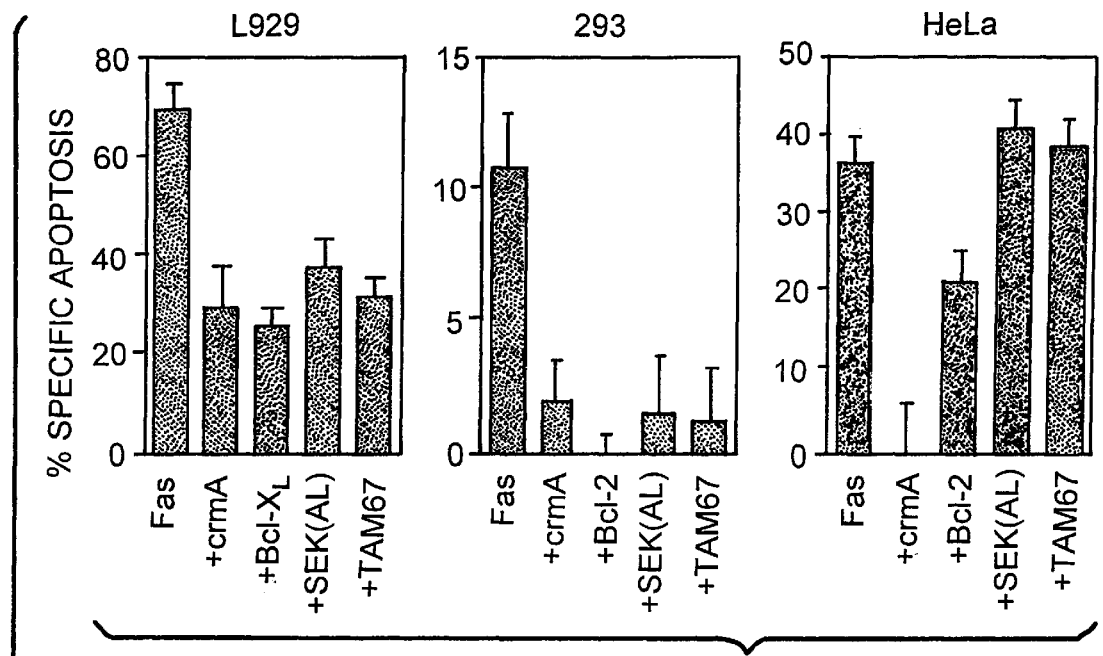
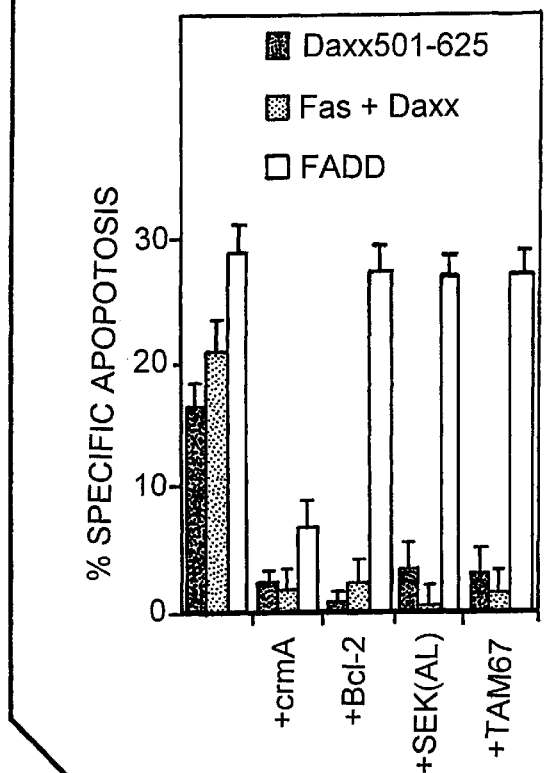
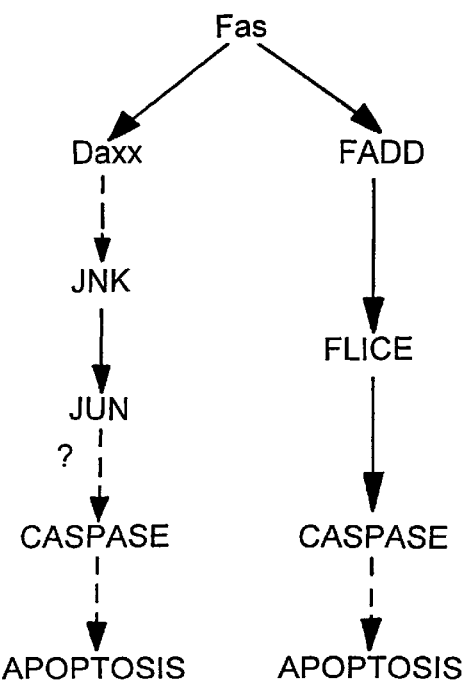
Fig. 8A
Fig. 8B
Fig. 8C
Fig. 8

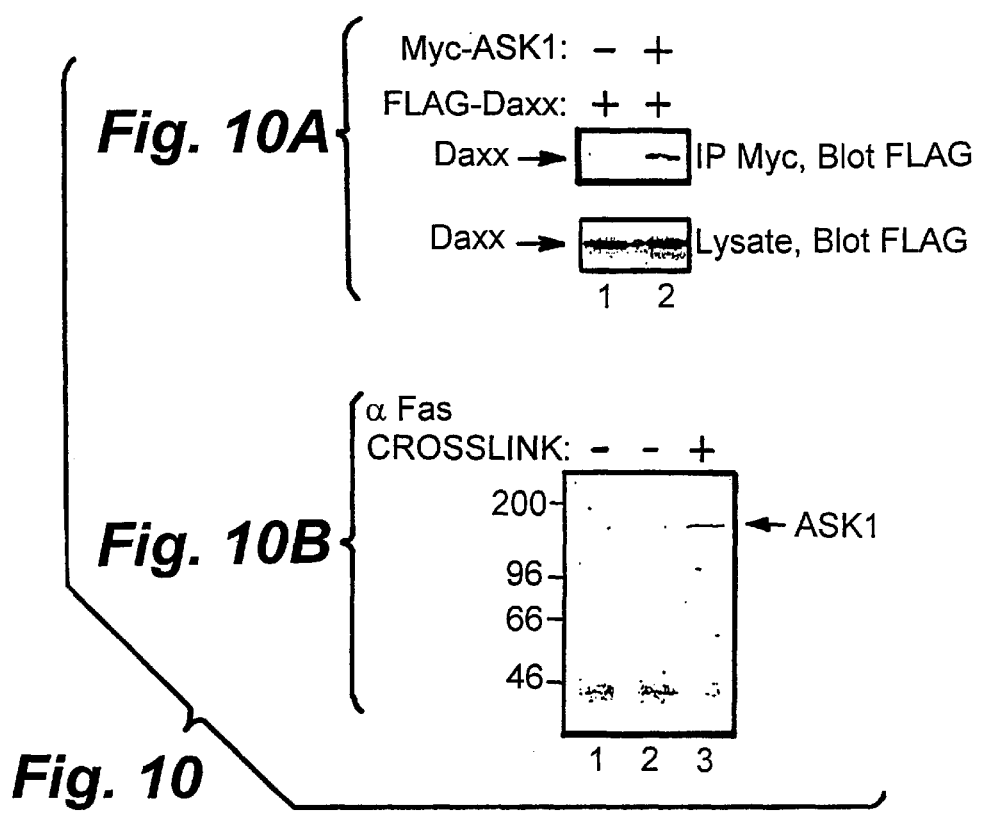

DAXX, A FAS-BINDING PROTEIN THAT ACTIVATES JNK AND APOPTOSIS

RELATED APPLICATIONS

This application claims benefit of U.S. provisional application Ser. No. 60/037,919, filed filed Feb. 12, 1997 and U.S. provisional application Ser. No. 60/051,753, filed filed Jun. 26, 1997.

GOVERNMENT SUPPORT

This work was funded in part by the National Cancer Institute under Grant No. CA51462-08. The Government may retain certain rights in this invention.

FIELD OF THE INVENTION

This invention relates to nucleic acids and encoded polypeptides which bind to Fas and potentiate Fas-mediated apoptosis. The invention also relates to agents which bind the nucleic acids or polypeptides. The invention further relates to methods of using such nucleic acids and polypeptides in the treatment and/or diagnosis of disease.

BACKGROUND OF THE INVENTION

Fas (also known as CD95 or APO-1) is a widely expressed cell death receptor that has a critical role in the regulation of the immune system and tissue homeostasis. Fas is activated by Fas ligand (FasL), a trimeric transmembrane protein (reviewed by Nagata, Cell 88:355–365, 1997). Fas is thought to have an essential role in deleting autoreactive lymphocytes and maintaining peripheral tolerance. Inherited Fas mutations in humans and mice cause a syndrome of massive lymphoproliferation and autoantibody production (reviewed by Nagata, 1997). Fas-induced apoptosis is also a major mechanism in cytotoxic T lymphocyte-mediated cytolysis and in the maintenance of immune privilege sites (reviewed by Abbas, Cell 84:655–658, 1996). Moreover, depending on the signal from the B cell antigen receptor, Fas may induce either apoptosis or proliferation of B cells in vivo (Rathmell et al., Cell 87:319–329, 1996).

Fas belongs to the tumor necrosis factor (TNF) receptor superfamily, which includes TNF receptor 1 (TNFR1), TNFR2, CD40, and the p75 low affinity NGF receptor; these receptors share characteristic cysteine-rich repeats in their extracellular domains (reviewed by Smith et al., Cell 76:959–962, 1994). The intracellular tails of Fas and TNFR1 share homologous death domains, an approximately eighty amino acid protein motif that is critical for signaling apoptosis (Itoh and Nagata, J. Biol. Chem. 268:10932–10937, 1993; Tartaglia et al., Cell 74:845–853, 1993). Over the last two years, elucidation of the mechanism for Fas-mediated apoptosis has begun (reviewed by Cleveland and Ihle, Cell 81:479–482, 1995; Fraser and Evan, Cell 85:781–784, 1996). FADD, also known as MORT1, is a cytoplasmic protein that has a C-terminal death domain which interacts with Fas and an N-terminal domain that can induce cell death (Chinnaiyan et al., Cell 81:505–512, 1995; Boldin et al., J. Biol. Chem. 270:7795–7798, 1995b). The N-terminus of FADD interacts with MACH/FLICE, an interleukin-1β converting enzyme (ICE) family cysteine protease (caspase) that potently induces apoptosis (Boldin et al., Cell 85:803–815, 1996; Muzio et al., Cell 85:817–827, 1996). Although the details are not yet clear, other caspases, including ICE and CPP32, are sequentially activated to execute the apoptotic dissolution of the cell (Enari et al., Nature 380:723–726, 1996). TNFR1 also interacts with FADD via an adaptor protein termed TRADD (Hsu et al., Cell 84:299–308, 1996). The emerging model from these molecular studies is that Fas, via FADD, directly engages and activates apoptotic ICE family proteases. However, this model fails to explain how Bcl-2 and other physiologic signals may modulate Fas-mediated apoptosis (Fraser and Evan, 1996). It remains possible that other signaling molecules in addition to FADD are involved in Fas-mediated apoptosis.

Fas can also activate the Jun N-terminal kinase/stress activated protein kinase (JNK/SAPK) pathway (Latinis and Koretzky, Blood 87:871–875, 1996; Lenczowski et. al., Mol. Cell. Biol. 17:170–181, 1997; Goillot et. al., Proc. Natl. Acad. Sci. USA 94:3302–3307, 1997). Analogous to the MAP kinase cascade, the prototypical JNK/SAPK pathway involves the sequential activation of the proteins MEKK1, SEK1, JNK, and c-Jun. Other targets of the JNK pathway include the transcription factors Elk-1 and ATF-2 (reviewed by Kyriakis and Avruch, Ann. N.Y. Acad. Sci. 766:303–319, 1996). This pathway was initially characterized by the ability of UV irradiation and transforming Ha-Ras to activate the AP-1 transcription factor; subsequently it was shown that TNF-α and other stress-activated signals may also activate this pathway. The significance of Fas-mediated JNK activation is currently unclear. One hypothesis is that activation of the JNK pathway contributes to Fas-mediated apoptosis (Goillot et. al., 1997). Dominant negative constituents of the JNK pathway can block stress- and TNF-induced apoptosis in several cell lines, suggesting that activation of JNK pathway is required for these apoptotic inducers (Verheij et al., Nature 380:75–79, 1996). Similarly, in PC12 cells that undergo apoptosis in response to nerve growth factor withdrawal, activation of the JNK pathway in concert with the suppression of the ERK pathway is critical to induce programmed cell death (Xia et al., Science 270:1326–1331, 1995). Alternatively, Fas-mediated JNK activation may drive cellular proliferation via activation of the proto-oncogene c-Jun and AP-1 transcriptional activity (Rathmell et al., Cell 87:319–329, 1996).

Recently, Liu et. al. have demonstrated that overexpression of FADD, the established downstream signal transducer of Fas, cannot activate JNK but that two other proteins engaged by TNFR1—RIP and TRAF2—are responsible for JNK activation by TNF (Liu et al., Cell 87:565–576, 1996). This raises the question of whether Fas also engages other proteins to activate the JNK pathway.

There exists a need to influence the Fas-mediated apoptosis and JNK signal transduction pathways to treat disease. There also exists a need to identify the gene(s) responsible for increased or decreased signal transduction and to provide therapies for treating diseases resulting from aberrant signal transduction.

SUMMARY OF THE INVENTION

We describe herein the molecular cloning and characterization of Daxx, a novel Fas binding protein. Daxx binds to the Fas death domain, yet lacks a death domain of its own. Overexpression of Daxx leads to JNK activation and potentiates Fas-induced apoptosis. The Fas binding domain of Daxx acts as a dominant negative inhibitor of Fas-induced apoptosis and JNK activation. Furthermore, using dominant negative and constitutively active forms of Daxx and FADD, we show that Fas engages two independent pathways to induce cell death: one pathway via Daxx that involves JNK activation and is blocked by Bcl-2, and a second pathway via FADD that is Bcl-2 insensitive.

The invention provides isolated nucleic acid molecules, unique fragments of those molecules, expression vectors containing the foregoing, and host cells transfected with those molecules. The invention also provides isolated polypeptides and agents which bind such polypeptides, including antibodies. The foregoing can be used in the diagnosis or treatment of conditions characterized by the expression of a Daxx nucleic acid or polypeptide. The invention also provides methods for identifying pharmacological agents useful in the diagnosis or treatment of such conditions. Here, we present the cDNA cloning of a 81.4 kDa Fas-associated protein, Daxx, a protein which potentiates Fas-mediated apoptosis.

According to one aspect of the invention, an isolated nucleic acid molecule is provided. The molecule hybridizes under stringent conditions to a molecule consisting of the nucleic acid sequence of SEQ ID NO:1. The isolated nucleic acid molecule codes for a polypeptide which binds to Fas. The invention further embraces nucleic acid molecules that differ from the foregoing isolated nucleic acid molecules in codon sequence to the degeneracy of the genetic code. The invention also embraces complements of the foregoing nucleic acids. In preferred embodiments, the isolated nucleic acid molecule comprises nucleotides 1-2358 of SEQ ID NO:1 or nucleotides 1-2340 of SEQ ID NO:4. In particularly preferred embodiments, the isolated nucleic acid molecule comprises nucleotides 25-2241 of SEQ ID NO:1 or nucleotides 1-2220 of SEQ ID NO:4.

Preferred isolated nucleic acid molecules are those comprising the human cDNAs or gene corresponding to SEQ ID NO:1. Preferably, the isolated nucleic acid molecule is a human homolog of the foregoing nucleic acid molecules and in some preferred embodiments comprises the nucleic acid sequence of SEQ ID NO:4. More preferably, the isolated nucleic acid molecule comprises a human homolog of molecule which encodes the polypeptide of SEQ ID NO:2 or SEQ ID NO:5.

According to another aspect of the invention, an isolated nucleic acid molecule is provided. The isolated nucleic acid molecule comprises a molecule consisting of a unique fragment of nucleotides 25-2441 of SEQ ID NO:1 between 12 and 2215 nucleotides in length, a molecule consisting of a unique fragment of nucleotides 1-2220 of SEQ ID NO:4 between 12 and 2119 nucleotides in length and complements thereof. In one embodiment, the isolated nucleic acid molecule consists of between 12 and 32 contiguous nucleotides of SEQ ID NO:1, SEQ ID NO:4, or complements of such nucleic acid molecules. In preferred embodiments, the unique fragment is at least 14, 15, 16, 17, 18, 20 or 22 contiguous nucleotides of the nucleic acid sequence of SEQ ID NO:1, SEQ ID NO:4, or complements thereof.

According to another aspect of the invention, the invention involves expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules. In preferred embodiments, the isolated polypeptide comprises a polypeptide having the sequence of SEQ ID NO:2 or SEQ ID NO:5. In other embodiments, the isolated polypeptide consists of a fragment or variant of the foregoing which retains the activity of the foregoing.

According to another aspect of the invention, there are provided isolated polypeptides which selectively bind a polypeptide encoded by the foregoing nucleic acids. Preferably the isolated polypeptides selectively bind a polypeptide which comprises the sequence of SEQ ID NO:2, SEQ ID NO:5, or fragments thereof.

According to another aspect of the invention, there are provided isolated polypeptides which selectively bind a complex of a first polypeptide, preferably a Daxx polypeptide or fragment thereof, bound to Fas. In certain embodiments the first polypeptide comprises the sequence of SEQ ID NO:2 or SEQ ID NO:5, and more preferably consists essentially of the sequence of SEQ ID NO:2 or SEQ ID NO:5. In preferred embodiments, the isolated binding polypeptides include antibodies and fragments of antibodies (e.g., Fab, F(ab)$_2$, Fd and antibody fragments which include a CDR3 region which binds selectively to the complex of the first polypeptide and Fas). According to still another aspect of the invention, methods for increasing or decreasing Fas-mediated apoptosis in a mammalian cell are provided. The methods involve administering to a mammalian cell an amount of Daxx-encoding nucleic acid or polypeptide, or an inhibitor of Daxx activity, effective to increase or decrease, respectively, Fas-mediated apoptosis in the mammalian cell. In certain embodiments, the inhibitor is a dominant negative fragment of Daxx polypeptide, especially the 112 C-terminal amino acids of SEQ ID NOs:2 or 5, or an antisense nucleic acid which inhibits the expression of Daxx.

According to still another aspect of the invention, methods for increasing or decreasing JNK signal transduction in a mammalian cell are provided. The methods involve administering to a mammalian cell an amount of Daxx-encoding nucleic acid or polypeptide, or an inhibitor of Daxx activity, effective to increase or decrease, respectively, JNK signal transduction in the mammalian cell. In certain embodiments, the inhibitor is a dominant negative fragment of Daxx polypeptide, especially the 112 C-terminal amino acids of SEQ ID NOs:2 or 5, or an antisense nucleic acid which inhibits the expression of Daxx.

The invention in another aspect provides compositions comprising an antisense nucleic acid which selectively binds to the nucleic acid of claim 1 and which reduces the expression of Daxx, and a pharmaceutically acceptable carrier.

The invention in a further aspect involves methods for increasing or decreasing Daxx-Fas or Daxx-ASK1 binding activity in a subject. An agent that selectively binds to an isolated nucleic acid molecule of the invention or an expression product thereof is administered to a subject in need of such treatment, in an amount effective to decrease Daxx-Fas or Daxx-ASK1 binding activity in the subject. Preferred agents are antisense nucleic acids, including modified nucleic acids, and polypeptides, such as a dominant negative variant of Daxx. For increasing Daxx-Fas or Daxx-ASK1 binding activity in a subject, an isolated nucleic acid molecule of the invention or an expression product thereof is administered to a subject in need of such treatment, in an amount effective to increase Daxx-Fas or Daxx-ASK1 binding activity in the subject.

According to another aspect of the invention, methods for decreasing Fas-mediated apoptosis in a cell are provided. The methods comprise contacting the cell with an amount of an agent which decreases the Fas-mediated apoptosis potentiating activity of Daxx effective to decrease Fas-mediated apoptosis in the cell. In certain embodiments, the agent is a vector which comprises a promoter active in the cell operably linked to a nucleic acid molecule selected from the group consisting of a nucleic acid molecule which encodes a Daxx dominant negative polypeptide, and a nucleic acid which encodes a Daxx antisense nucleic acid molecule. In other embodiments, the agent is a Daxx antisense oligonucleotide. In still other embodiments, the agent is a compound which inhibits the binding of Daxx to a polypeptide selected from the group consisting of Fas and ASK1.

According to still another aspect of the invention, methods for increasing apoptosis in a cell are provided. The methods comprise contacting the cell with an amount of an agent which increases apoptosis in the cell, wherein the agent is selected from the group consisting of a vector which expresses Daxx, or a fragment thereof which has Fas-mediated apoptosis-inducing activity, a Daxx polypeptide, or a fragment thereof which has Fas-mediated apoptosis-inducing activity, a vector which expresses a fragment of Daxx polypeptide which has constitutive apoptosis activity, and a fragment of Daxx polypeptide which has constitutive apoptosis activity. In embociments wherein the agent is a vector which expresses a fragment of Daxx polypeptide which has constitutive apoptosis activity or a fragment of Daxx polypeptide which has constitutive apoptosis activity, the fragment of Daxx polypeptide which has constitutive apoptosis activity preferably is selected from group consisting of DaxxDC, DaxxC501, and Daxx 501-625.

The invention in another aspect provides methods for treating a condition characterized by abnormal Fas-mediated apoptosis. Such methods comprise administering to a subject having the condition an amount of an agent which decreases the Fas apoptosis potentiating activity of Daxx effective to reduce Fas-mediated apoptosis in the subject. Preferably the agent is a vector which comprises a promoter active in the tissue affected by the condition operably linked to a nucleic acid molecule selected from the group consisting of a nucleic acid molecule which encodes a Daxx dominant negative polypeptide, and a nucleic acid which encodes a Daxx antisense nucleic acid molecule. In other preferred embodiments the agent is a Daxx antisense oligonucleotide or a compound which inhibits the binding of Daxx to a polypeptide selected from the group consisting of Fas and ASK1. In certain embodiments of the foregoing methods, the condition is selected from the group consisting of 1) allograft tissue rejection, 2) graft-versus-host disease, 3) fulminant hepatitis, and 4) cancers which increase the amount of Fas apoptosis, including NK lymphoma and large granular lymphocytic leukemia. In other embodiments of the foregoing methods, the condition is apoptosis of T cells (e.g. by immune privileged cells such as tumor cells) and the agent is delivered to T cells.

In yet another aspect of the invention, methods for treating a condition characterized by insufficient apoptosis are provided. The methods comprise administering to a subject having the condition an amount of an agent which increases Daxx apoptosis activity effective to increase apoptosis in the subject. In certain embodiments, the condition is characterized by insufficient Fas-mediated apoptosis, and the agent increases Fas-mediated apoptosis activity of Daxx effective to increase Fas-mediated apoptosis in the subject; preferred embodiments include those wherein the condition is selected from the group consisting of septic shock/sepsis, autoimmune disease including autoimmune lymphoproliferative syndrome, liver hyperplasia and abnormal lymphoproliferation including lymphoma. In other preferred embodiments, the agent is selected from the group consisting of a Daxx polypeptide and a vector having a promoter operably linked to Daxx nucleic acid.

The invention also provides methods for diagnosing a disorder characterized by aberrant expression of a Daxx nucleic acid molecule or an expression product thereof. Such methods comprise contacting a biological sample isolated from a subject suspected to have the disorder with an agent that binds to the Daxx nucleic acid molecule or an expression product thereof. In such methods, the nucleic acid molecule is one which hybridizes under stringent conditions to a molecule selected from the group consisting of the nucleic acid sequence of SEQ ID NO: 1, and the nucleic acid sequence of SEQ ID NO:4. The methods further comprise detecting the binding between the agent and the Daxx nucleic acid molecule or the expression product thereof in the sample to obtain a first result and comparing the first result with a control result as a diagnostic measure of the disorder. Preferably the agent is a nucleic acid molecule selected from the group consisting of a nucleic acid molecule having the nucleotide sequence of SEQ ID NO:1, a nucleic acid molecule having the nucleotide sequence of SEQ ID NO:4, unique fragments thereof, and complements thereof, or comprises a CDR3 region of an antibody. In embodiments in which the agent is a nucleic acid molecule, the interaction preferably is determined by amplifying at least a portion of the Daxx nucleic acid.

According to another aspect of the invention, methods are provided for identifying lead compounds for a pharmacological agent useful in the diagnosis or treatment of disease associated with Daxx Fas binding activity. The methods involve forming a mixture of a Daxx polypeptide or fragment thereof containing a Fas death domain binding site, a protein which interacts with the foregoing Fas death domain binding site, and a candidate pharmacological agent. The mixture is incubated under conditions which, in the absence of the candidate pharmacological agent, permit a first amount of selective binding of the protein which interacts with the Daxx Fas death domain binding site by the Daxx polypeptide containing a Fas death domain binding site. A test amount of selective binding of the protein which interacts with the Daxx Fas death domain binding site by the Daxx polypeptide containing a Fas death domain binding site then is detected. Detection of an increase in the test amount of selective binding of the Fas death domain by the Daxx polypeptide containing a Fas death domain binding site in the presence of the candidate pharmacological agent relative to the first amount indicates that the candidate pharmacological agent is a lead compound for a pharmacological agent which increases selective binding of the Fas death domain by the Daxx polypeptide containing a Fas death domain binding site. Detection of a decrease in the foregoing activity in the presence of the candidate pharmacological agent indicates that the candidate pharmacological agent is a lead compound for a pharmacological agent which decreases selective binding of the Fas death domain by the Daxx polypeptide containing a Fas death domain binding site. Preferably the protein containing a Fas death domain binding site is a Daxx polypeptide which comprises the amino acid sequence of the 112 C-terminal amino acids of SEQ ID NO:2 or of SEQ ID NO:5. Similar methods are provided for identifying lead compounds for a pharmacological agent which reduces or enhances Daxx protein binding to ASK1.

According to another aspect of the invention, a method for diagnosing a disorder characterized by aberrant Fas apoptosis or JNK signal transduction is provided. The method includes contacting a biological sample isolated from a subject suspected of having the disorder with a first agent that binds to a first protein selected from the group consisting of Daxx, Fas and ASK1. The method also includes the step of isolating a protein complex bound to the first agent, such as by immunoprecipitation, electrophoresis, chromatography and the like. The method also includes determining the proteins in the protein complex as a determination of the disorder. Where the complex does not include Daxx and Fas or ASK1, the subject can be diagnosed as having the disorder. Preferably the step of determining the proteins in the protein complex includes contacting the protein complex with a second agent that binds to a second protein selected from the group consisting of Daxx, Fas and ASK1, wherein the second protein is not the first protein. In certain embodiments of the foregoing methods, the first agent and/or the second agent is an antibody.

The invention also contemplates specifically the use of the compositions in the manufacture of a medicament, particularly medicaments for treating conditions characterized by elevated or reduced levels of apoptosis.

Thus an object of the invention is to provide compounds that desirably influence the Fas-mediated apoptosis and JNK signal transduction pathways.

Another object of the invention is to provide therapeutics for treating diseases resulting from aberrant apoptosis and JNK signal transduction.

Still another object of the invention is to provide diagnostics and research tools relating to Daxx, Fas and JNK.

These and other objects of the invention will be described in further detail in connection with the detailed description of the invention.

BRIEF DESCRIPTION OF THE DRAWINGS

FIG. 2 shows Daxx sequence and mRNA distribution. FIG. 2A depicts the predicted amino acid sequence of Daxx protein. FIG. 2B is a Northern blot which shows the tissue distribution of Daxx.

FIG. 3 depicts the interaction of Daxx with Fas in vitro and in mammalian cells. FIG. 3A shows binding of in vitro translated $^{35}$S-Daxx to GST-fusion proteins. FIG. 3B depicts binding of full length and truncated $^{35}$S-Daxx to GST and GST-FasDD. FIG. 3C depicts the association of HA-Daxx and HA-DaxxDC with the GST fusion of Fas intracellular tail (GST-FasIC) in 293 cells.

FIG. 4 shows that Daxx potentiates Fas-induced apoptosis. FIG. 4A shows the morphology of normal and apoptotic 293 and HeLa cells. FIG. 4B demonstrates that Daxx potentiates Fas-induced apoptosis in 293 cells. FIG. 4C shows that Daxx potentiates Fas-induced apoptosis in HeLa cells. FIG. 4D demonstrates that L929 cells stably overexpressing Daxx have accelerated specific apoptosis in response to Fas.

FIG. 5 shows that Daxx activates the JNK pathway. FIG. 5A shows that Daxx induces JNK activation in transient transfection. FIG. 5B demonstrates that stable expression of Daxx constitutively activates JNK. FIG. 5C shows that Daxx activates a JNK-dependent reporter gene.

FIG. 6 relates deletion analysis of Daxx. FIG. 6A shows apoptosis and JNK activation by Daxx deletion mutants. FIG. 6B shows that DaxxC inhibits Fas-induced apoptosis. FIG. 6C shows that DaxxC inhibits Fas-induced JNK activation.

FIG. 7 shows that Daxx and FADD activate distinct apoptotic pathways. FIG. 7A shows the inhibition of Fas-induced apoptosis by DaxxC and FADD(80-205). FIG. 7B shows that FADD(80-205) fails to inhibit Fas-induced JNK activation. FIG. 7C shows that DaxxC does not inhibit FADD-mediated apoptosis.

FIG. 8 depicts the inhibition profile of Daxx- and FADD-induced apoptosis. FIG. 8A shows the inhibition profile of Fas-induced apoptosis in L929, 293, and HeLa cells. FIG. 8B shows the inhibition of profile of Fas+Daxx, Daxx501-625 and FADD in 293 cells. FIG. 8C depicts two pathways of Fas signaling that induce cell death.

FIG. 9 shows that a Fas mutant from autoimmune lymphoproliferative syndrome has a selective defect in Daxx binding. FIG. 9A shows the binding of Fas wildtype and mutant proteins to Daxx and FADD. FIG. 9B shows the equal expression of the proteins in the experimental system.

FIG. 10 shows that Daxx interacts with ASK1 and recruits ASK1 to Fas. FIG. 10A shows that Daxx binds ASK1 in mammalian cells. FIG. 10B shows that endogenous ASK1 is recruited to Fas in a ligand-dependent manner.

BRIEF DESCRIPTION OF THE SEQUENCES

Figures 1, 1A, 1B, 1C:
FIG. 1 shows the interaction of clone A and Daxx with Fas death domain in yeast.
FIG. 1A is a schematic representation of the cytoplasmic domain of murine Fas.
FIG. 1B shows interaction in the two-hybrid system.
FIG. 1C shows that the C-terminus of clone A interacts with Fas death domain.

SEQ ID NO:1 is the nucleotide sequence of the mouse Daxx cDNA (GenBank accession number AF006040).

SEQ ID NO:2 is the amino acid sequence encoded by the mouse Daxx cDNA.

SEQ ID NO:3 is the partial nucleotide sequence of the human Daxx cDNA (GenBank accession number AF006041).

SEQ ID NO:4 is the complete nucleotide sequence of the human Daxx cDNA.

SEQ ID NO:5 is the amino acid sequence encoded by the human Daxx cDNA.

DETAILED DESCRIPTION OF THE INVENTION

The present invention in one aspect involves the cloning of a cDNA encoding a Daxx Fas binding protein. The sequence of the mouse gene is presented as SEQ ID NO:1, and the predicted amino acid sequence of this gene's protein product is presented as SEQ ID NO:2. The sequence of the human gene is presented as SEQ ID NO:4, and the predicted amino acid sequence of this gene's protein product is presented as SEQ ID NO:5. Analysis of the sequence by comparison to nucleic acid and protein databases determined that Daxx is a completely novel protein with no significant sequence similarity to death domains or other protein motifs.

The invention thus involves in one aspect Daxx polypeptides, genes encoding those polypeptides, functional modifications and variants of the foregoing, useful fragments of the foregoing, as well as therapeutics relating thereto.

Homologs and alleles of the Daxx nucleic acids of the invention can be identified by conventional techniques. Thus, an aspect of the invention is those nucleic acid sequences which code for Daxx polypeptides and which hybridize to a nucleic acid molecule consisting of the coding region of SEQ ID NO:1 or SEQ ID NO:4, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Daxx nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

In screening for Daxx proteins, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the expression of the Daxx gene is abundant in mouse tissues, and given the teachings herein of a near-ftull-length human Daxx cDNA clone it is likely that the human cDNA clone corresponding to the mouse Daxx gene can be isolated from a human cDNA library prepared from one or more of the tissues in which Daxx expression is abundant, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Daxx polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or SEQ ID NO:4 or complements of thereof. A unique fragment is one that is a 'signature' for the larger nucleic acid. It, for example, is long enough to assure that its precise sequence is not found in molecules outside of the Daxx nucleic acids defined above. Unique fragments can be used as probes in Southern blot assays to identify such nucleic acids, or can be used in amplification assays such as those employing PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the Daxx polypeptides, useful, for example, in immunoassays or as a competitive binding partner of the Fas and/or other polypeptides which bind to the Daxx polypeptides, for example, in therapeutic applications. Unique fragments further can be used as antisense molecules to inhibit the expression of Daxx nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NO:1 or SEQ ID NO:4 and complements will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). Virtually any segment of the region of SEQ ID NO:1 beginning at nucleotide 25 and ending at nucleotide 2241, or SEQ ID NO:4 beginning at nucleotide 1 and ending at nucleotide 2220, or complements thereof, that is 18 or more nucleotides in length will be unique. Those skilled in the art are well versed in methods for selecting such sequences, typically on the basis of the ability of the unique fragment to selectively distinguish the sequence of interest from non-Daxx nucleic acids. A comparison of the sequence of the fragment to those on known data bases typically is all that is necessary, although in vitro confirmatory hybridization and sequencing analysis may be performed.

As mentioned above, the invention embraces antisense oligonucleotides that selectively bind to a nucleic acid molecule encoding a Daxx polypeptide, to decrease Fas binding by Daxx. This is desirable in virtually any medical condition wherein a reduction in Fas binding activity of Daxx is desirable, including to reduce apoptosis. Antisense Daxx molecules, in this manner, can be used to slow down or arrest the proliferation of cancer cells in vivo.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, SEQ ID NO:4, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., Nature Biotechnol. 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., Cell Mol. Neurobiol. 14(5):439–457, 1994) and at which proteins are not expected to bind. Finally, although, SEQ ID Nos: 1 and 3 disclose a cDNA sequences, one of ordinary skill in the art may easily derive the genomic DNA corresponding to these sequences. Thus, the present invention also provides for antisense oligonucleotides which are complementary to the genomic DNA corresponding to SEQ ID NO:1 and/or SEQ ID NO:4. Similarly, antisense to allelic or homologous Daxx cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding Daxx polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding Daxx polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of Daxx gene "knock-outs" in cells and in animals, providing materials for studying certain aspects of Fas binding activity and signal transduction.

The invention also provides isolated polypeptides, which include the polypeptide of SEQ ID NO:2, the polypeptide of SEQ ID NO:5, and unique fragments therof. Such polypeptides are useful, for example, alone or as fusion proteins to generate antibodies, as a components of an immunoassay.

A unique fragment of an Daxx polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 or SEQ ID NO:5 will require longer segments to be unique while others will require only short segments, typically between 5 and 12 amino acids (e.g. 5, 6, 7, 8, 9, 10, 11 and 12 amino acids long). Virtually any segment of SEQ ID NO:2 or SEQ ID NO:5 that is 10 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding of nucleic acids or proteins, and enzymatic activity. Those skilled in the art are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The invention embraces variants of the Daxx polypeptides described above. As used herein, a "variant" of a Daxx polypeptide is a polypeptide which contains one or more modifications to the primary amino acid sequence of a Daxx polypeptide. Modifications which create a Daxx variant can be made to a Daxx polypeptide 1) to reduce or eliminate an activity of a Daxx polypeptide, such as Fas binding or stimulation of JNK activity; 2) to enhance a property of a Daxx polypeptide, such as protein stability in an expression system or the stability of protein-protein binding; or 3) to provide a novel activity or property to a Daxx polypeptide, such as addition of an anti genic epitope as provided in the Examples, or addition of a detectable moiety. Modifications to a Daxx polypeptide are typically made to the nucleic acid which encodes the Daxx polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Daxx amino acid sequence.

Variants can include Daxx polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a Daxx polypeptide by eliminating proteolysis by proteases in an expression system (e.g., dibasic amino acid residues in yeast expression systems in which KEX2 protease activity is present).

Mutations of a nucleic acid which encode a Daxx polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Daxx polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a Daxx gene or cDNA clone to enhance expression of the polypeptide.

The skilled artisan will realize that conservative amino acid substitutions may be made in Daxx polypeptides to provide functionally equivalent variants of the foregoing polypeptides, i.e, the variants retain the functional capabilities of the Daxx polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the Daxx polypeptides include conservative amino acid substitutions of SEQ ID NO:2 and/or SEQ ID NO:5, particularly conservative substitutions of amino acids other than the 101 or 112 C-terminal amino acids of SEQ ID NO:2 and/or SEQ ID NO:5, which include sequences which are sufficient for Daxx binding to Fas. However, conservative substitutions of those amino acids can be made as well. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of Daxx polypeptides, i.e., variants of Daxx polypeptides which retain the function of the natural Daxx polypeptides, are contemplated by the invention. Conservative amino-acid substitutions in the amino acid sequence of Daxx polypeptides to produce functionally equivalent variants of Daxx polypeptides typically are made by alteration of a nucleic acid encoding Daxx polypeptides (SEQ ID Nos:1, 3). Such substitutions can be made by a variety of methods known to one of ordinary skill in the art. For example, amino acid substitutions may be made by PCR-directed mutation, site-directed mutagenesis according to the method of Kennel (Kennel, *Proc. Nat. Acad. Sci. U.S.A.* 82:488–492, 1985), or by chemical synthesis of a gene encoding a Daxx polypeptide. The activity of functionally equivalent fragments of Daxx polypeptides can be tested by cloning the gene encoding the altered Daxx polypeptide into a bacterial or mammalian expression vector, introducing the vector into an appropriate host cell, expressing the altered Daxx polypeptide, and testing for a functional capability of the Daxx polypeptides as disclosed herein.

Thus the invention also provides, in certain embodiments, "dominant negative" polypeptides derived from SEQ ID NO:2 and/or SEQ ID NO:5. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of a Daxx polypeptide, one of ordinary skill in the art can modify the sequence of the Daxx polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity (e.g., activation of apoptosis or the JNK pathway) and for retention of a desired activity (e.g., Fas binding activity of Daxx). Other similar methods for creating and testing dominant negative variants of a protein will be apparent to one of ordinary skill in the art.

Dominant negative Daxx proteins include variants in which a portion of the amino terminus of the Daxx protein has been mutated or deleted to reduce or eliminate downstream effects of Daxx-Fas binding, i.e. enhanced Fas-mediated apoptosis. For example, the C-terminal portion of Daxx (e.g., the 112 C-terminal amino acids of SEQ ID NO:2) can bind to Fas, and acts as a dominant negative inhibitor of Fas-induced apoptosis and JNK activation (see Examples below).

The invention as described herein has a number of uses, some of which are described elsewhere herein. First, the invention permits isolation of Daxx polypeptides. A variety of methodologies well-known to the skilled practitioner can be utilized to obtain isolated Daxx molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of Daxx mRNA in cell-free extracts such as the reticulocyte lysate system also may be used to produce Daxx polypeptides. Those skilled in the art also can readily follow known methods for isolating Daxx polypeptides. These include, but are not limited to, immunochromotography, HPLC, size-exclusion chromatography, ion-exchange chromatography and immune-affinity chromatography.

The isolation of the Daxx cDNA also makes it possible for the artisan to diagnose a disorder characterized by expression of Daxx. These methods involve determining expression of the Daxx gene, and/or Daxx polypeptides derived therefrom. In the former situation, such determinations can be carried out via any standard nucleic acid determination assay, including the polymerase chain reaction, or assaying with labeled hybridization probes as exemplified below.

The invention also makes it possible isolate proteins having particular Daxx binding domains, such as Fas and TNFRI, by the binding of such proteins to Fas death domain binding sequences present in the Daxx polypeptide, as disclosed herein. The identification of the Fas binding site of Daxx also permits one of skill in the art to block the binding of a protein having a death domain, such as Fas, with a binding partner having a Fas binding site, such as Daxx or a fragment of Daxx which retains the Fas binding site. For example, binding of the proteins can be effected by introducing into a biological system in which the proteins bind (e.g., a cell) a polypeptide including a Fas binding site in an amount sufficient to block the binding of Daxx to Fas. The identification of the Fas binding site in Daxx also enables one of skill in the art to prepare modified proteins, using standard recombinant DNA techniques, which can bind to proteins containing a Fas death domain. For example, when one desires to target a certain protein to the inner membrane surface where proteins containing a death domain, such as Fas, are localized, one can prepare a fusion polypeptide of the certain protein and the Daxx Fas binding site. Other proteins selectively bind to additional binding sites located in the Daxx polypeptide. These include proteins which activate the JNK pathway.

The invention also involves agents such as polypeptides which bind to Daxx and to complexes of Daxx polypeptides and their binding partners. Such binding agents can be used, for example, in screening assays to detect the presence or absence of Daxx polypeptides and complexes of Daxx polypeptides and their binding partners and in purification protocols to isolate Daxx polypeptides and complexes of Daxx polypeptides and their binding partners. Such agents also can be used to inhibit the native activity of the Daxx polypeptides or their binding partners, for example, by binding to such polypeptides, or their binding partners or both.

The invention, therefore, embraces peptide binding agents which, for example, can be antibodies or fragments of antibodies having the ability to selectively bind to Daxx polypeptides alone or in a complex with a binding partner such as Fas. Antibodies include polyclonal and monoclonal antibodies, prepared according to conventional methodology. Where antibodies which bind a complex of a Daxx polypeptide and a binding partner, such as Fas, are desired, the complex is used as the immunogen for preparation of the antibody. The complex can be cross-linked according to standard protein cross-linking techniques to provide a stable molecule as the immunogen. Thus an antibody which bind the complex are preferably those antibodies which recognize epitopes on both the Daxx polypeptide and binding partner components of the complex. Alternatively, complex-specific antibodies can be those antibodies which recognize an epitope on one of the complex components which is specific to the conformation of the component in the complex. For example, Daxx may assume a preferred conformation when bound to Fas which creates one or more antigenic epitopes not present in the unbound Daxx polypeptide.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Daxx polypeptides, and complexes of both Daxx polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Daxx polypeptide or a complex of Daxx and a binding partner such as Fas. This process can be repeated through several cycles of reselection of phage that bind to the Daxx polypeptide or complex. Repeated rounds lead to enrichment of phage bearing particular sequences. DNA sequence analysis can be conducted to identify the sequences of the expressed polypeptides. The minimal linear portion of the sequence that binds to the Daxx polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the Daxx polypeptides. Thus, the Daxx polypeptides of the invention, or a fragment thereof, or complexes of Daxx and a binding partner can be used to screen peptide libraries, including phage display libraries, to identify and select peptide binding partners of the Daxx polypeptides of the invention. Such molecules can be used, as described, for screening assays, for purification protocols, for interfering directly with the functioning of Daxx and for other purposes that will be apparent to those of ordinary skill in the art.

A Daxx polypeptide, or a fragment which contains Fas binding site, also can be used to isolate their native binding partners, including, e.g., the Fas protein that complexes with Daxx. Isolation of binding partners may be according to well-known methods. For example, isolated Daxx polypeptides can be attached to a substrate, and then a solution suspected of containing Fas protein may be applied to the substrate. If the binding partner for Daxx polypeptides is present in the solution, then it will bind to the substrate-bound Daxx polypeptide. The binding partner then may be isolated. Other proteins which are binding partners for Daxx, such as other proteins which contain Fas death domains may be isolated by similar methods without undue experimentation.

It will also be recognized that the invention embraces the use of the Daxx cDNA sequences in expression vectors, as well as to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The expression vectors require that the pertinent sequence, i.e., those nucleic acids described supra, be operably linked to a promoter.

The invention further provides methods for reducing or increasing Fas-mediated apoptosis in a cell. Such methods are useful in vitro for altering Fas-mediated apoptosis, for example, in testing compounds for potential to block aberrant Fas-mediated apoptosis. In preferred embodiments, the methods involve contacting the cell with an agent which modulates the Fas-mediated apoptosis potentiating activity of Daxx in an amount effective to modulate such apoptosis, i.e., to increase or decrease Fas-mediated apoptosis. As used herein, "Fas-mediated apoptosis potentiating activity of Daxx" or "Daxx Fas-mediated apoptosis potentiating activity" means the effect which Daxx has on the apoptotic processes induced by Fas. As demonstrated herein, Daxx potentiates Fas-mediated apoptosis (and Fas-mediated JNK activation). Increasing Fas-mediated apoptosis in a cell by, e.g., introducing a Daxx polypeptide in the cell, or decreasing Fas-mediated apoptosis in a cell by, e.g., introducing a dominant negative Daxx polypeptide or Daxx antisense nucleic acid in the cell, can be used to provide a model system for testing compounds which affect Fas-mediated apoptosis. Such methods also are useful in the treatment of conditions which result from excessive or deficient Fas-mediated apoptosis. As known in the art, and as shown in the Examples, Fas-mediated apoptosis can be measured readily by determining membrane blebbing, pyknosis, cell body condensation, and nuclear fragmentation as judged by Hoechst staining. Other methods will also be known to one of skill in the art.

The agent for modulation of Fas-mediated apoptosis will be different for increasing or decreasing Fas-mediated apoptosis. For example, in methods for decreasing Fas-mediated apoptosis, agents include compounds which reduce the effect of Daxx, including Daxx dominant negative polypeptides, such as fragments of Daxx which bind to Fas but do not transduce the apoptotic signal, and anti-Daxx antibodies. Agents also include compounds which reduce the expression of Daxx, such as antisense Daxx nucleic acids including oligonucleotides. The skilled artisan will understand that identification of such agents can proceed via standard methods of the art. For example, to determine the effect of antisense Daxx nucleic acid molecules, one can contact a Daxx-expressing cell with such molecules and detemine the expression of Daxx before and after the contacting. A reduction in Daxx nucleic acid or polypeptide expression indicates that the antisense molecule effectively reduced the expression of Daxx and thus would be a candidate for an agent for decreasing Fas-mediated apoptosis. Identification of Daxx fragments which modulate Fas-mediated apoptosis can include assays such as determining the binding of Daxx to Fas in the presence and the absence of such Daxx fragments. Daxx fragments which reduce the binding of Daxx and Fas are candidates for agents which reduce the effect of Daxx on Fas-mediated apoptosis. Other similar methods standard to the molecular biology and drug discovery arts can also be employed to identify agents for modulating the effects of Daxx on Fas-mediated apoptosis. Thus, the "agent" is not limited to nucleic acids and polypeptides, but also embraces small molecules which could interfere with, or enhance, the effects of Daxx on Fas-mediated apoptosis.

Methods for increasing apoptosis in a cell are also provided. In these methods, a cell is contacted with an agent which increases apoptosis in the cell. For these methods, an agents include Daxx polypeptides which potentiate Fas-mediated apoptosis and nucleic acids encoding such polypeptides, and also Daxx polypeptides which have consitutive apoptosis-inducing activity (e.g., which do not require Fas/Fas-L binding for apoptosis) and nucleic acids encoding such polypeptides. In particular, the latter Daxx molecules, those which have constitutive apoptotic activity, include DaxxDC, DaxxC501 and Daxx501-625. Methods for identifying other such agents are provided herein, such as the methods described for identification of Fas-mediated apoptosis modulating agents above, and in the Examples below. One of ordinary skill in the art will understand that standard methods of molecular biology which are used for determining the fragments of polypeptides and nucleic acids that have a certain activity can be used to further dissect Daxx for fragments which have constitutive apoptosis activity. Such methods include mutagenesis, including site-directed mutagenesis, preparation of fragments by restriction endonuclease or exonuclease digestion, and the like, followed by expression of the Daxx fragment and testing for constitutive apoptosis activity as described above for Fas-mediated apoptosis.

The foregoing agents which modulate the effect of Daxx on Fas-mediated apoptosis can also be used in the treatment of conditions characterized by abnormal Fas-mediated apoptosis. The methods involve administering to a subject having such a condition an amount of an agent which decreases the Fas-mediated apoptosis potentiating activity of Daxx effective to reduce the Fas-mediated apoptosis.

Several conditions have been identified which result from abnormal Fas-mediated apoptosis. These conditions include: allograft tissue rejection in which the allograft is destroyed by apoptosis (Smyth et al., *Transplantation* 62:1529–1532, 1996), graft-versus-host disease (Via et al., *J. Immunol.* 157:5387–5393, 1996; Baker et al., *Proc. Acad. Nat'l. Sci. USA* 94:1366–1371, 1997), fulminant hepatitis (Ogasawara et al., *Nature*, 364:806–809, 1993; Tanaka et al., *J. Immunol.* 158:2303–2309, 1997), and certain cancers, including NK lymphoma and large granular lymphocytic leukemia (Tanaka et al., *Nature Med.* 2:317–322, 1996). Other conditions which result from Fas-mediated apoptosis can be identified by the methods employed to identify the foregoing conditions. In general, such methods can include assays of apoptosis in cells derived from such subjects, in the presence and in the absence of compounds which block Fas activity. Other assays will be known to those skilled in the art. For conditions in which reduced Fas-mediated apoptosis results in a disease state, such as septic shock/sepsis, autoimmune disease resulting from a lack of elimination of B cells which produce autoantibodies (Elkon et al, *Curr. Opin. Immunol.* 8:852–859, 1996), liver hyperplasia (Adachi et al., *Nat. Genet.* 11:294–300, 1995), and abnormal lymphoproliferation (see Nagata, 1997 and references therein), agents which increase Fas-mediated apoptosis, or which have constitutive apoptotic activity, can be administered. Such agents are described in greater detail above and in the Examples below.

The subject can be monitored before, during and/or after administering an agent to modulate the effect of Daxx on Fas-mediated apoptosis. Various parameters can be monitored, such as the modulation of Fas-mediated apoptosis, the reduced or increased synthesis and/or steady state levels of Daxx, and the relevant clinical parameters of the particular condition. Methods for measuring apoptosis have been extensively described in the literature, both for in vitro model systems and in connection with conditions resulting from aberrant Fas-mediated apoptosis. Methods for measuring Daxx nucleic acids and/or polypeptides are set forth herein.

Still other methods are provided for diagnosing disorders which are characterized by aberrant expression of Daxx nucleic acid molecule or encoded polypeptide. The methods of diagnosis include contacting a biological sample from a subject suspected of having the disorder with an agent that binds to the Daxx nucleic acid molecule or polypeptide. In these methods, an agent includes molecules such as nucleic acids which hybridize under stringent conditions to the Daxx nucleic acids in the biological sample, and molecules such as antibodies or fragments thereof which bind to Daxx polypeptides. The process of contacting the agent with the biological sample can include other method steps which are standard in the art of sample analysis, such as detergent solubilization, homogenization, purification, sedimentation, enzymatic digestion, and the like.

The diagnosis methods also include a step of detecting the binding of the agent to the Daxx nucleic acid of polypeptide which gives a first result for that sample. Detection methods are well known in the art and are amenable to automation. Detection can be based on properties of the Daxx molecule, such as size or weight, or can be based on properties of the agent as bound to the Daxx molecule, including fluorescence, radioactivity, color, enzymatic activity and the like. Detection also embraces amplification of all or a portion of a Daxx molecule in combination with the agent, such as by polymerase chain reaction, ligase chain reaction, and the like.

The result of the detection step (the first result) is then compared with a control result to provide a diagnostic measure of the disorder. For comparisons in which the first result is greater than the control result, the diagnosis would indicate increased expression of Daxx. For comparisons in which the first result is lesser than the control result, the diagnosis would indicate decreased expression of Daxx. Additional diagnostic methods relate to determining the proteins present in Daxx protein complexes. As shown herein, Daxx binds to Fas and to ASK1. In certain conditions, the Daxx pathway is disrupted at the Fas-Daxx or Daxx-ASK1 binding step. Thus, for example, determining Daxx-Fas or Daxx-ASK1 binding can be predictive of such disorders. It is also possible to diagnose subsets of such disorders by examining the binding of FADD to Fas. As shown herein, certain Fas mutants bind to FADD but not Daxx, while other Fas mutants fail to bind to FADD and Daxx. The former mutants are found in autoimmune patients who also have a high correlation of lymphomas. Thus, by examining these protein interactions, one can diagnose the disorder and also predict the outcome of the disorder, thereby permitting treatment which is better suited to a particular subject.

The invention further provides methods for reducing or increasing JNK signal transduction in a cell. Such methods are useful in vitro for altering the JNK signal transduction, for example, in testing compounds for potential to block aberrant JNK signal transduction. Increasing JNK signal transduction in a cell by, e.g., introducing a Daxx polypeptide in the cell, or decreasing JNK signal transduction in a cell by, e.g., introducing a dominant negative Daxx polypeptide or Daxx antisense nucleic acid in the cell, can be used to provide a model system for testing compounds which affect JNK signal transduction. Such methods also are useful in the treatment of conditions which result from excessive or deficient JNK signal transduction. As known in the art, JNK signal transduction can be measured by determining phosphorylation of c-Jun or transcription stimulation from a SRF-dependent promoter element. Other methods will also be known to one of skill in the art.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, produces the desired response. In the case of treating a condition characterized by abnormal apoptosis (an increased or decreased level of apoptosis relative to normal), the desired response is modulating the apoptosis (reducing or enhancing the level of apoptosis) to achieve a level of apoptosis which alleviates the condition. This may involve only slowing the progression of the disease temporarily, although more preferably, it involves halting the progression of the disease permanently. This can be monitored by routine methods or can be monitored according to diagnostic methods of the invention discussed herein.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of screening compounds for agents active at the level of a cellular function modulated by Daxx or a Daxx fragment. In particular, such functions include Fas-mediated apoptosis, JNK signal transduction, and formation of a Daxx-Fas protein complex or a Daxx-ASK1 protein complex. Generally, the screening methods involve assaying for compounds which interfere with a Daxx activity such as Daxx-Fas or Daxx-ASK1 binding, etc. Such methods are adaptable to automated, high throughput screening of compounds. The target indications for agents detected by the screening methods are limited only in that the target cellular function be subject to modulation by alteration of the formation of a complex comprising a Daxx polypeptide or fragment thereof and one or more natural Daxx intracellular binding targets, such as Fas or other protein including a Fas death domain. Target indications include cellular processes modulated by JNK, Fas, and other Fas death domain-containing proteins described above.

A wide variety of assays for compounds are provided, including, labeled in vitro protein-protein binding assays, immunoassays, cell-based assays such as two- or three-hybrid screens, expression assays, etc. For example, three-hybrid screens are used to rapidly examine the effect of transfected nucleic acids on the intracellular binding of Daxx or Daxx fragments to specific binding partners such as Fas or ASK1. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a Fas-binding Daxx polypeptide fused to a GAL4 DNA binding domain and a nucleic acid encoding a Fas protein including a death domain fused to a transcription activation domain such as VP16. The cell also contains a reporter gene operably linked to a gene expression regulatory region, such as one or more GAL4 binding sites. Activation of reporter gene transcription occurs when the Daxx and Fas fusion polypeptides bind such that the GAL4 DNA binding domain and the VP16 transcriptional activation domain are brought into proximity to enable transcription of the reporter gene. Compounds which modulate a Daxx-Fas binding are then detected through a change in the expression of reporter gene. Methods for determining changes in the expression of a reporter gene are known in the art. Similar assays for Daxx-ASK1 binding also are provided.

Daxx and/or fragments used in the methods, when not produced by a transfected nucleic acid are added to an assay mixture as an isolated polypeptide. Daxx polypeptides preferably are produced recombinantly, although such polypeptides may be isolated from biological extracts. Recombinantly produced Daxx polypeptides include chimeric proteins comprising a fusion of a Daxx protein with another polypeptide, e.g., a polypeptide capable of providing or enhancing protein-protein binding, sequence specific nucleic acid binding (such as GAL4), enhancing stability of the Daxx polypeptide under assay conditions, or providing a detectable moiety, such as green fluorescent protein. A polypeptide fused to a Daxx polypeptide or fragment may also provide means of readily detecting the fusion protein, e.g., by immunological recognition or by fluorescent labeling.

The assay mixture is comprised of a natural intracellular Daxx binding target (e.g. a Daxx binding partner such as a Fas protein or ASK1). While natural Daxx binding targets may be used, it is frequently preferred to use portions (e.g., peptides or nucleic acid fragments) or analogs of the Daxx binding target (i.e., agents which mimic the Daxx binding properties of the natural binding target for purposes of the assay) so long as the portion or analog provides binding affinity and avidity to the Daxx fragment measurable in the assay.

The assay mixture also comprises a compound. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate compounds encompass numerous chemical classes, although typically they are organic compounds. Preferably, the candidate compounds are small organic compounds, i.e., those having a molecular weight of more than 50 yet less than about 2500, preferably less than about 1000 and, more preferably, less than about 500. Candidate compounds comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compounds is a nucleic acid, the agent typically is a DNA or RNA molecule, although modified nucleic acids as defined herein are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, bacterial flagella peptide display libraries and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known compounds may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, anti-microbial agents, and the like may also be used.

The mixture of the foregoing assay materials is incubated under conditions whereby, but for the presence of the candidate compound, the Daxx polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the Daxx polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting the materials contained in a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of Daxx polypeptide binding to a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a Daxx binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides Daxx-specific binding agents, methods of identifying and making such agents, and their use in diagnosis, therapy and pharmaceutical development. For example, Daxx-specific agents are useful in a variety of diagnostic and therapeutic applications, especially where disease or disease prognosis is associated with improper utilization of a pathway involving Daxx, e.g., JNK activation, Fas-Daxx complex formation, etc. Novel Daxx-specific binding agents include Daxx-specific antibodies and other natural intracellular binding agents identified with assays such as two hybrid screens, and non-natural intracellular binding agents identified in screens of chemical libraries and the like.

In general, the specificity of Daxx binding to a binding agent is shown by binding equilibrium constants. Targets which are capable of selectively binding a Daxx polypeptide preferably have binding equilibrium constants of at least about $10^7$ $M^{-1}$, more preferably at least about $10^8$ $M^{-1}$, and most preferably at least about $10^9$ $M^{-1}$. The wide variety of cell based and cell free assays may be used to demonstrate Daxx-specific binding. Cell based assays include one, two and three hybrid screens, assays in which Daxx-mediated transcription is inhibited or increased, etc. Cell free assays include Daxx-protein binding assays, immunoassays, etc. Other assays useful for screening agents which bind Daxx polypeptides include fluorescence resonance energy transfer (FRET).

Various techniques may be employed for introducing nucleic acids of the invention into cells, depending on whether the nucleic acids are introduced in vitro or in vivo in a host. Such techniques include transfection of nucleic acid-CaPO$_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

EXAMPLES

Experimental Procedures
Reagents and Cell Lines
Anti-murine Fas Jo2 antibody was the generous gift of S. Nagata (Ogasawara et al., Nature 364:806–809, 1993). Murine TNF-α (Genzyme, Cambridge, Mass.), monoclonal antibody M2 against Flag epitope (Kodak/IBI), and anti-JNK-1 antibody C17 (Santa Cruz Biotech, Santa Cruz, Calif.) were obtained from the indicated sources. HeLa, 293, and L929 were obtained originally from American Type Culture Collection (ATCC, Rockville, Md.). To establish the L/Daxx cell line, HA-Daxx vector was cotransfected with pBabe-puro into L929 cells using lipofectamine-mediated gene transfer (GIBCO-BRL, Gaithersburg, Md.). Resistant cells were selected in media containing 2.5 μg/ml of puromycin. Positive clones were identified by immunoblot analysis using anti-HA antibody 12CA9. The L929 cells expressing mFas (L/Fas) were established by transfecting pRc/CMV-mFas into L929 cells and subsequently selecting for resistant cells in 600 μg/ml G418. Resistant clones were then screened for Fas expression by FACScan using Jo2 antibody.

Plasmid Construction

DNA fragments for most plasmid constructs were obtained by PCR amplification using Pfu polymerase (Stratagene, La Jolla, Calif.) and primers incorporated with appropriate restriction sites and epitope tags as needed. The fragments for LexA and transcription activator fusions were cloned into plasmid pEG202 and pJG4-5 (Gyuris et al., Cell 75:791–803, 1993), respectively. The I225N mutation in LexA-lpr$^{cg}$ was made by site-directed mutagenesis using a two-step PCR protocol (Higuchi et al., Nucleic Acids Res. 16:7351–7367, 1988). GST constructs were made in pGEX vector (Pharmacia, Piscataway, N.J.). In vitro translation constructs were made in pET3a (Novagen, Madison, Wis.) or pBluescript (Stratagene). Daxx(-162) was obtained by digestion of a full length Daxx construct with HindIII. For expressing proteins in mammalian cells, full length Daxx and FADD, and mutants thereof, were cloned into pEBB, a derivative of pEF-BOS (Mizushima and Nagata, Nucleic Acids Res. 18:5322, 1990), with a hemagglutinin (HA) epitope-tag at the 5' end. Full length murine Fas was cloned into pEBB and pRc/CMV (Invitrogen, Carlsbad, Calif.). Fas intracellular region (amino acids 165 to 306) was fused to GST in pEBG, a derivative of pEBB expressing GST. Full length murine TNFR1 was cloned in pEBB. Each construct was confirmed by restriction digestion, partial DNA sequence, and for plasmids expressing proteins in yeast and mammalian cells, by immunoblot analysis.

The following plasmids were described in or obtained from the indicated sources: LexA-CD40IC(Cheng et al., Science 267:1494–1498, 1995), p18-34 and LexA-Bicoid (Gyuris et al., 1993), pHD1.2 (crmA) and pBabe-Bcl-2 (J. Yuan, Harvard University, Cambridge, Mass.), Bcl-XL (R. J. Lutz, Apoptosis, Inc.), TAM67 and Flag-JNK (M. Karin, UCSD, San Diego, Calif.), pEBG-SEK(AL) (C. J. Der, UNC, Charlotte, N.C.), SRE-L-Luc (R. Treisman, ICRF, UK).

Two-hybrid Screen and β-Galactosidase Assay

The two-hybrid screen was performed essentially as described (Gyuris et al., 1993). Among 1×10$^6$ library plasmids screened, 33 interacting clones were obtained. The cDNA inserts of the library plasmids within those colonies were isolated directly from yeast by PCR and were grouped based on restriction digestion and cross-hybridization. Representative plasmids from each group were recovered from yeast and transformed back into yeast to test their interaction with different baits.

For assaying β-galactosidase expression, each pair of DNA-binding (LexA) and activation hybrids were co-transfected together the lacZ reporter plasmid p18-34 (Gyuris et al., 1993) into EGY48 yeast cells. Filter lift assay for colony color and quantitative liquid assay were done as described (Yang et al., *EMBO J.* 13:5878–5886, 1994) for three to six independent transformants.

cDNA Cloning and Northern Blot Analysis

The cDNA insert in clone A21 was used to screen $6 \times 10^5$ pfu of a murine spleen cDNA library (Stratagene) following a standard protocol (Sambrook et al., 1989) and eight clones were recovered. Sequence analysis shown that they were derived from the same gene but apparently lacked its 5' end. The N-terminal sequence of the longest positive clone was then used to screen $5 \times 10^5$ and $1 \times 10^5$ pfu of murine brain (Stratagene) and thymus cDNA libraries (Y. W. Choi, Rockefeller University, New York, N.Y.), respectively. Sequences of the longest cDNA clone (2.4 kb) from the thymus library as well as the cDNA inserts of clone A21 were determined on both strands with an automated sequencer (Applied Biosystems, Foster City, Calif.).

For Northern analysis, the C-terminal 0.7 kb fragment of murine Daxx and a human β-actin cDNA (Clontech, Palo Alto, Calif.) were used to probe a mouse multiple tissue Northern blot (Clontech), according to the manufacturer's protocol.

In Vitro Binding and Coprecipitation Assays

Glutathione-S-transferase (GST) fusions were purified as described (Smith and Johnson, 1988). $^{35}$S-proteins were made with TNT Reticulocyte Lysate System (Promega, Madison, Wis.). $^{35}$S-proteins were incubated with 10 mg of each GST fusion protein in 0.1 ml modified E1A buffer (Hsu et. al., *Cell* 81: 495–504, 1995) with 50 mM NaCl and 10% glycerol for 1–2 hours, pelleted by pulse microcentrifugation, washed three times, and analyzed by SDS-PAGE and autoradiography. A fraction of the reaction mixture was analyzed by Coomassie staining to visualize GST fusion proteins.

For testing association in mammalian cells, HA-Daxx and HA-DaxxDC were cotransfected with GST-FasIC or GST into 293 cells by calcium phosphate method. Thirty-six hours after cotransfection, cells were solubilized in E1A buffer, precipitated with glutathione beads (Molecular Probes, Eugene, Oreg.), washed 3 times with E1A buffer, and immunoblotted for HA. Immunoblots were developed with the appropriate secondary antibodies and visualized by ECL (Amersham, Arlington Heights, Ill.). Comparable levels of GST fusions and HA-Daxx proteins in 293 cell extracts were verified by immunoblotting.

Apoptosis Assays

Cells were plated onto 6-well dishes the day before transfection at $2 \times 10^5$ cells/well for HeLa and 293 cells and $5 \times 10^5$ for L/Daxx and L/EBB cells. The wells were pre-coated with 0.2% gelatin for 293 cells. HeLa and 293 cells were transfected by the calcium phosphate precipitation method and L/Daxx and L/EBB with lipofectamine (GIBCO-BRL). X-gal staining was done for 4 hours to overnight. The percentage of apoptotic cells was determined by the number of blue cells with apoptotic morphology divided by the total number of blue cells. Specific apoptosis was calculated as the percentage of blue cells with apoptotic morphology in each experimental condition minus the percentage of blue cells with apoptotic morphology in pEBB vector-transfected cells. pEBB vector control transfection was always done in parallel and had about 5 percent or less apoptotic cells. At least 400 cells from 4 random fields were counted in each experiment and the data shown are the average and SD of at least three independent experiments.

For L929 apoptosis assay in FIG. 8, $2.5 \times 10^5$ cells/well of L/Fas cells were seeded in 6-well plates. On the next day cells were co-transfected with 200 ng of pHook-1 plasmid (Invitrogen) and 400 ng of crmA, Bcl-xL or SEK (AL) with lipofectamine. The pHook-1 construct expresses a single chain antibody (sFv) against the hapten phOx, which allows selection of transfected cells by using phOx-conjugated magnetic beads. Twenty four hours after transfection cells were removed from the dish in 1 ml of PBS/3 mM EDTA. Magnetic beads ($1.5 \times 10^6$) were added to the cells and incubated at 37° C. for 30 min. The cells were then washed 3 times in media, counted and plated in duplicate in 96 well plates (~5000 cells/well). After culture for 14–16 hours, Fas-killing was induced using Jo2 antibody (1 μg/ml) and 0.5 μg/ml of actinomycin D and measured by counting the number of surviving cells in four random fields 24 hours later. Efficiency of transfection and cell selection were monitored by cotransfection of pCMV-lacZ.

JNK Activity and Reporter Gene Assays

HeLa and 293 cells were transfected in 60 mm dishes with Flag-JNK plus the indicated expression plasmids by the calcium phosphate method. Approximately 24 hours after transfection cells were serum starved for 14–16 hours. Cells transfected with Fas were treated with 0.5 mg/ml of Jo2 antibody for 30 min. To test for the effect of protease inhibitors, cells were treated with 0.5 mg/ml of Jo2 and 100 mM of ICE inhibitor Z-Val-Ala-Asp-CH2F or CPP32 inhibitor Z-Asp-Glu-Val-Asp-CH2F (Enzyme Systems Products, Calif.) for 30 min. JNK-1 was immunoprecipitated with anti-Flag antibody, and in vitro kinase assay with 1 μg of GST-cJun (1–79) was performed as previously described (Khosravi-Far et al., *Mol. Cell. Biol.* 16:3923–3933, 1996). The kinase reaction was then stopped with 2×SDS polyacrylamide gel electrophoresis (SDS-PAGE) loading buffer. Proteins were separated on 15% SDS-PAGE in duplicate gels. One set was stained to check for equivalent GST-cJun loading. This gel was then dried and exposed to film for 4–6 hours. Another gel was immunoblotted with anti-FLAG antibody to visualize expression of JNK-1.

JNK1 kinase activity in L929 cells stably expressing Fas or Daxx was measured by immunoprecipitation of the endogenous JNK-1 using anti-JNK-1 C-17 antibody. TNFR1- and Fas-transfected cells were treated with 20 ng/ml TNF-α for 10 minutes and 0.5 μg/ml Jo2 for 30 minutes, respectively. The kinase assay was then carried out as described above.

SRE-L reporter gene assay: 293 cells were cotransfected with 1 μg of the indicated plasmids with 1 μg of SRE-L-Luc reporter construct (Hill et al., *Cell* 81:1159–1170, 1995). After an incubation of 24 hours, cells were switched to 0.5% FCS media for 14–16 hours. Cell lysates were prepared in 250 μl reporter lysis buffer (Promega) and 20 ml of the lysate was assayed in Luminometer with 100 μl ATP and Luciferin reagents (Promega) as described (Khosravi-Far et al., 1996).

Example 1

Two-hybrid Screen for Novel Fas Interacting Proteins

To identify novel Fas interacting proteins, we performed a two-hybrid screen with the death domain of murine Fas fused to the DNA binding protein LexA (LexA-mFasDD). A plasmid library of fusions between a transcription activator domain and cDNAs from human HeLa cells was screened for interaction with LexA-mFasDD in a yeast reporter strain. LexA constructs containing the indicated amino acids (in parenthesis) of receptors expressed similar level of fusion proteins in yeast. Colony color and β-galactosidase units were determined as described in the Experimental Procedures. One group of positive interactors, typified by clone A21, interacted strongly with FasDD. However, it interacted poorly with either Fas-lp$^{cg}$, an Ile224Asn mutation in the Fas death domain which abrogates Fas signaling and causes lymphoproliferation in mice (reviewed by Nagata, 1997) or with Fas-FD8, a functionally inactive deletion mutation of the Fas death domain (Itoh and Nagata, 1993) (FIG. 1B). Sequence analysis of clone A21 revealed it to encode a portion of a novel protein. The activation hybrid Act-DaxxC501 contains amino acids 501 to 739 of Daxx.

In the two-hybrid system, clone A21 also interacted with the intracellular domain of human Fas and the death domain of TNFR1, but not with the intracellular region of CD40, a closely related receptor that lacks a death domain (FIG. 1B). The sequence C-terminal to the Fas death domain has been shown to inhibit the cytotoxicity of Fas death domain (Itoh and Nagata, 1993) and it also inhibits the binding of FADD to Fas (Chinnaiyan et al., 1995). The presence of this inhibitory region had no effect on the binding of clone A21 to Fas because clone A21 interacted equally well with FasDD and FasIC (FIG. 1B).

We mapped the Fas interaction domain on Clone A21 to the C-terminal 112 amino acids by deletion analysis (FIG. 1C). Amino acids contained in each activation hybrids are indicated. This region showed no evident sequence similarity to death domains, suggesting that the interaction between clone A21 and Fas is not through a homotypic death domain association.

Example 2
Cloning of Daxx cDNA and Northern Analysis

Using clone A21 as the probe, we cloned a cross-hybridizing full length murine cDNA (SEQ ID NO:1). Sequence analysis revealed an open reading frame able to encode a protein of 739 amino acids (SEQ ID NO:2) with a predicted molecular mass of 81.4 kDa (FIG. 2A). The C-terminus of this protein is homologous to clone A21. The open reading frame of murine Daxx follows an in-frame stop codon and begins with a Kozak consensus sequence. The regions enriched for acidic residues and proline are underlined. The partial human cDNA sequence from A21 (SEQ ID NO: 3) is shown below the mouse sequence. Identical amino acids between mouse and human sequences are indicated by "-". The full length human Daxx cDNA was also cloned and sequenced (SEQ ID NO: 5). We call this gene Daxx for Fas death domain associated protein. A database search using BLAST revealed that Daxx is a novel protein with no significant sequence similarity to any other protein. Daxx contains a region of 62 amino acids with a high content (71%) of glutamic acid and aspartic acid and contains two small proline-rich regions (FIG. 2A).

To determine the tissue distribution of Daxx, we performed a Northern analysis with a Daxx C-terminal probe. A mouse multiple tissue Northern blot was probed with a C-terminal 0.7 kb fragment of Daxx and a human β-actin cDNA. A 2.6 kb transcript, consistent with the length of the open reading frame, was detected in various adult mouse tissues (FIG. 2B). The expression of Daxx appeared uniform, with the exception of stronger expression in testis. Shorter hybridizing transcripts were also detected in liver, kidney, and testis. Cell lines from many tissues have been reported to support the ability of ectopically expressed Fas to induce apoptosis, suggesting that the downstream signaling mechanism is present in most tissues. Similarly, FADD is expressed ubiquitously in adult tissues (Boldin et al., 1995b; Chinnaiyan et al., 1995).

Example 3
Daxx Interacts with Fas Both in vitro and in vivo

In the two-hybrid system, the Daxx C-terminal region interacted strongly with Fas, confirming that Daxx is the functional homolog of clone A21 (FIG. 1B). We then tested the binding of full length murine Daxx protein in vitro and in mammalian cells. In vitro translated, $^{35}$S-labeled Daxx bound to immobilized glutathione S-transferase (GST) fusion proteins of Fas death domain and TNFR1 intracellular tail but not to immobilized GST or GST-CD40 intracellular tail or GST-Fas lpr$^{cg}$ death domain (FIG. 3A). Positions of MW standards (in kDa) are shown at left. Coomassie stained GST fusion proteins from the same gel were aligned to show protein levels. Daxx migrated with an apparent molecular weight of approximately 120 kDa on SDS-PAGE; this slower than expected migration may reflect the high content of acidic residues in Daxx. In the GST pull-down assay, $^{35}$S-Daxx bound to GST-FasDD but only very weakly to GST-TNFR1. This discrepancy with the two-hybrid result (FIG. 1) may be due to the nonlinear readout of the two-hybrid system. Deletion of 162 amino acids from the C-terminus of Daxx abrogated binding to GST-FasDD while the C-terminal 112 amino acids (DaxxC) was sufficient to bind GST-FasDD (FIG. 3B), consistent with the two-hybrid results. Daxx(-162) was missing C-terminal 162 aa of Daxx; DaxxC corresponded to aa 628-739. Input of $^{35}$S-Daxx and $^{35}$S-Daxx(-162) proteins in binding assays are shown in lane 1 and 2, respectively. GST fusion proteins are shown on the bottom panel.

To determine whether Daxx interacted with Fas in mammalian cells, human embryonic kidney 293 cells were cotransfected with constructs expressing hemagglutinin-tagged Daxx (HA-Daxx) and GST-Fas intracellular tail (GST-FasIC). The presence of HA-Daxx and HA-DaxxDC in extracts was verified by immunoblotting for HA (bottom panel, FIG. 3C). HA-Daxx was coprecipitated with GST-FasIC but not with GST by glutathione beads. Again, this interaction was dependent on the C-terminus of Daxx (FIG. 3C). GST-FasIC was also able to coprecipitate HA-tagged Fas death domain, confirming that death domains may multimerize. Because Fas is overexpressed and thereby activated, we are uncertain whether Daxx binds to the inactive Fas. Collectively, these data show that the C-terminus of Daxx mediates an interaction between the Fas death domain and Daxx, and that this interaction is likely to occur directly and in vivo.

Example 4
Daxx Potentiates Fas-mediated Apoptosis

To study the role of Daxx in Fas signaling, we chose 293 cells and HeLa cells. Both are sensitive to Fas- and TNF-mediated apoptosis, and their normally flat morphology facilitates the scoring of apoptotic cells, characterized by membrane blebbing, pyknosis, and cell body condensation (FIG. 4A). Cells scored to be apoptotic by morphology also exhibited nuclear condensation and fragmentation as judged by Hoechst staining. HeLa and 293 cells were transiently transfected with various expression constructs (as indicated) and an expression construct for β-galactosidase; at defined times after the transfection, cells were stained for β-galactosidase activity to mark the transfected cells and scored for apoptotic morphology. In 293 cells, transient overexpression of Fas induced apoptosis in a dose-dependent and saturable manner (FIG. 4B). Indicated amount (in μg) of pEBB-Fas and pEBB-HA-Daxx plasmids were cotransfected with 0.5 μg of pCMV-lacZ. The total amount of transfected DNA was made constant by adding vector DNA. The cells were stained with X-gal 20 hours after transfection and analyzed for apoptotic morphology as described in the Experimental Procedures above. Fas activation in the absence of activating ligand is due to a documented propensity of death domains to multimerize (Boldin et al., *J. Biol. Chem.* 270:387–391, 1995a).

However, the addition of activating anti-Fas antibodies, Jo2, did not increase cell death in Fas-transfected 293 cells, implying that a function downstream of receptor activation may be limiting. Overexpression of Daxx by itself did not induce apoptosis, but Daxx coexpression significantly enhanced Fas-mediated apoptosis (FIG. 4B). Parallel experiments with TNFR1 did not show any enhancement of apoptosis by Daxx, consistent with the much lower affinity of Daxx for TNFR1 (FIG. 3A).

In HeLa cells, transient transfection of Fas led to robust, dose-dependent and saturable cell death (FIG. 4A, C), which was further enhanced by the addition of Jo2. Transfection and specific apoptosis were done and measured as in 293 cells except that X-gal staining was done at 24 hrs after transfection. As in 293 cells, overexpression of Daxx alone did not induce apoptosis in HeLa cells. In the range where apoptosis is proportional to input Fas DNA, coexpression of Daxx significantly increased Fas-mediated apoptosis (FIG. 4C), suggesting that Daxx activity may be a rate limiting step downstream of receptor engagement.

In an analogous approach to assess the function of Daxx, we established murine fibroblast L929 cell lines that stably overexpress Daxx (L/Daxx). L/Daxx cells are substantially more susceptible to Fas killing compared to vector transfected cells (L/EBB). L/EBB and L/Daxx were transfected with 1 $\mu$g of pEBB-Fas, pEBB-TNFR1, or pRK-FADD plus 0.2 $\mu$g of pCMV-lacZ. Specific apoptosis was determined as in FIG. 4B at indicated time after transfection. Similar results were obtained with multiple L/Daxx lines. This stimulation effect appeared to be a kinetic one: the L/Daxx culture had greater than three-fold more apoptotic cells 24 hours after Fas transfection compared to L/EBB, but L/EBB cells caught up by 48 hours after transfection (FIG. 4D). TNF-$\alpha$-, TNFR1-, or FADD-mediated apoptosis was not increased in L/Daxx cells (FIG. 4D and not shown). Therefore, L/Daxx cells are not generally more sensitive to apoptosis, but are specifically sensitized to the Fas signal, suggesting that Daxx is a mediator of Fas-induced killing.

Example 5
Daxx Activates the JNK/SAPK Pathway

The lack of death domain homology or constitutive cell death activity suggests that Daxx may play a different role from previously identified death domain binding proteins in Fas signaling. Fas has been reported to activate the JNK pathway (Latinis and Koretzky, 1996), which is required in certain cell lines for the analogous TNF-$\alpha$-induced apoptosis (Verheij et al., 1996). We therefore analyzed the ability of Fas and Daxx to activate the kinase activity of JNK and JNK-dependent transcription. In transient transfection assays in 293 cells, Fas activated JNK-1, the major JNK activity in cells (Derijard et al., Cell 76:1025–1037, 1994). Flag-tagged JNK1 (Flag-JNK) and the indicated plasmids (1 $\mu$g each) were cotransfected into 293 cells. Fas-induced JNK activation was not blocked by the serpin ICE inhibitor crmA (FIG. SA), a peptide ICE inhibitor Z-VAD, or a peptide CPP32 inhibitor Z-DEVD. FADD overexpression did not induce JNK (FIG. 5A). Therefore Fas activation of JNK is not secondary to FADD activity or apoptosis. Interestingly, Daxx overexpression activated JNK-1 to a level similar to that of Fas (FIG. 5A). To assay endogenous JNK activation by Fas and Dax, we used L929 cells stably expressing murine Fas (L/Fas) and the L/Daxx and L/EBB cells. In L/Fas cells, Fas-induced JNK activation was observed approximately 15 minutes after Fas ligation and reached maximal activity in about one hour (FIG. 5A). L/Daxx cells had constitutive activation of JNK activity compared to L/EBB cells (FIG. 5B), and the level of JNK activation correlated with the level of Daxx overexpression in various L/Daxx cell lines.

As an independent measure of JNK activity, we tested the ability of Fas and Daxx to stimulate signaling to SRF (Serum Response Factor). JNK can phosphorylate and activate SRF independent of the MEK/MAPK pathway, and the level of JNK activation in vivo can be assayed using a reporter gene driven by SRE-L, a derivative of SRE that specifically binds SRF (Hill et. al., 1995). In 293 cells, Fas induced SRF-dependent transcription about 4-fold, and Daxx induced it about 6-fold. TNF-$\alpha$, a known inducer of the JNK pathway, stimulated the SRF-reporter gene to a level similar to that induced by Fas or Daxx (FIG. 5C).

Collectively, these data show that Daxx is an activator of the JNK pathway.

Example 6
Deletion Mutagenesis of Daxx

To further dissect Daxx signaling, we asked which regions of Daxx were required for its three activities: Fas binding, enhancement of apoptosis, and activation of JNK. We have already determined that the C-terminal 112 amino acids of Daxx (DaxxC) are necessary and sufficient for Fas binding (FIG. 3B). Significantly, Daxx mutants missing either the C-terminus (DaxxDC) or N-terminus 500 amino acids (DaxxC501) acquired a modest constitutive cell death activity for 293 cells in the absence of Fas (FIG. 6A). Apoptosis assay: 3 $\mu$g of each Daxx mutant construct was transfected into 293 cells as above. HeLa cells and L929 cells were not sensitive to this activity. The result in 293 cells suggested that deletion of either end of Daxx activated a normally latent cell death activity. Because DaxxDC is unable to bind Fas death domain (FIGS. 3B and 3C), this cell death activity is likely to be independent of Fas or other death domain proteins. Further deletions revealed that amino acids 501 to 625, which lie immediately N-terminal to the Fas binding domain, contained most of the cell death activity (FIG. 6A).

An assay of JNK activation was performed: transient transfection of 1 $\mu$g of each Daxx mutant construct or pEBB vector (v) with 1 $\mu$g of Flag-JNK and in vitro JNK assay was done as above. Equal Flag-JNK expression was verified by immunoblotting for Flag. When these Daxx mutants were tested for their ability to activate JNK, we observed that each deletion mutant maintained some level of JNK activity with the exception of DaxxC; the majority of the activity came from just the region with amino acids 501-625 (FIG. 6A). This result suggests that JNK activation may be involved in Daxx-stimulated apoptosis. However, full length Daxx activates JNK but does not cause constitutive apoptosis, suggesting that full length Daxx may activate other pathways that counterbalance the apoptotic JNK signal.

Example 7
DaxxC Is a Dominant Negative Inhibitor of Fas-mediated Apoptosis and JNK Activation Deletion mutagenesis showed that DaxxC, the C-terminal 112 amino acids of Daxx, was necessary and sufficient to bind Fas but more N-terminal domains were required to activate JNK and cell death. Thus, we tested whether DaxxC can act as a dominant negative inhibitor of endogenous Daxx by competing with its binding to Fas. We chose to use HeLa cells in these experiments because the cells have a robust response to transfected Fas (FIG. 4C) and are the source of clone A21 from the two-hybrid screen. HeLa cells were transfected with 0.5 $\mu$g pEBB-Fas and pCMV-lacZ and the indicated amount (in $\mu$g) of HA-Daxx and HA-DaxxC. Total amount of transfected DNA was made constant by adding pEBB. Jo2 (12.5 ng/ml) was added 16 hrs later. X-gal staining was done at 24 hrs after transfection. In FIG. 6B, we show that expression of DaxxC gave a dose-dependent suppression of Fas-mediated apoptosis. Fas-induced c-Jun phosphorylation was also inhibited by DaxxC in HeLa cells (transient transfection of 1 μg of each indicated plasmid with 1 μg of Flag-JNK and in vitro JNK assay was done as above) and in 293 cells (FIG. 6C). To address the specificity of DaxxC, we then coexpressed full-length Daxx with DaxxC and asked if this combination now reversed the dominant negative effect. If DaxxC were binding other death domain containing proteins (e.g. FADD), coexpression of full length Daxx would further titrate FADD away from Fas and inhibit apoptosis. Instead, coexpression of Daxx with Fas and DaxxC gave a dose-dependent rescue of Fas-induced apoptosis (FIG. 6B). This result argues that the only functions made deficient by DaxxC are those of intact Daxx, implying that DaxxC specifically competes with endogenous Daxx but not other proteins for binding to Fas. These results suggest that endogenous Daxx is required for Fas-induced apoptosis and JNK activation.

Example 8
Daxx and FADD Define Two Distinct Fas-Mediated Signaling Pathways

Because Daxx and FADD are both required for Fas-induced apoptosis, we assessed how these two effectors may be related to each other by a dominant negative approach. The FADD death domain, FADD(80-205), has been shown to block Fas-induced death presumably by preventing the binding of endogenous FADD (Chinnaiyan et al., 1996). HeLa cells were transfected with 0.5 μg of pEBB-Fas, pCMV-lacZ, and plasmids (in μg) expressing the indicated proteins. Jo2 (12.5 ng/ml) was added 16 hrs later; X-gal staining was done 24 hrs after transfection. JNK kinase activity was assayed after transient transfection of 2 μg of each of the indicated plasmids with 2 μg of Flag-JNK. We found that FADD(80-205) partially inhibited Fas-induced death (FIG. 7A, lanes 1–3) but did not inhibit JNK activation (FIG. 7B). Moreover, the effect of FADD(80-205) on cell death was not reversed by coexpression of excess Daxx (FIG. 7A, lane 4). These results contrast with the effects of DaxxC (FIG. 6) and suggest that Daxx and FADD bind independently to Fas and activate distinct pathways. Consistent with this interpretation, FADD-induced cell death is not blocked by DaxxC (FIG. 7C). HeLa cells were transfected with the indicated amount (in μg) of FADD and DaxxC and assayed as FIG. 4C. HeLa cells were transfected with the indicated amount (in μg) of FADD and DaxxC and assayed as described above. In addition, DaxxC plus FADD (80-205) inhibited Fas-induced cell death substantially more than saturating amounts of either dominant negative protein alone (FIG. 7A, lane 7). Thus, Daxx and FADD activate apoptosis downstream of Fas by distinct but cooperative pathways.

Fas-mediated apoptosis can be inhibited by crmA and, in some cell types, by Bcl-2, a negative regulator of cell death (Enari et al., Nature 375:78–81, 1995; Los et al., Nature 375:81–83, 1995; Tewari and Dixit, J. Biol. Chem. 270:3255–3260, 1995; Itoh et al., J. Immunol. 151:621–627, 1993; Lacronique et. al., Nature Med. 2:80–86, 1996). To dissect the apoptotic pathways initiated by overexpression of Fas, Daxx, and FADD, the ability of crmA, Bcl-2, SEK(AL) and TAM67 to block each apoptotic inducer was tested. SEK(AL) and TAM67 are dominant negative inhibitors of the JNK pathway. SEK1 is the kinase that phosphorylates and activates JNK; SEK(AL) encodes a mutant that has a single mutation at the ATP-binding site, abrogating the kinase activity (Sanchez et al., Nature 372:794–798, 1994).

TAM67 is a variant of c-Jun in which amino acids 3-122 have been deleted. This mutant can dimerize and bind DNA but lacks a transcriptional activation domain (Brown et al., Oncogene 9791–799, 1994). First, the ability of the panel of inhibitor genes to block Fas was tested in several cell types commonly used in apoptosis studies. Transfection and apoptosis analysis in L/Fas cells were performed as described above. 293 cells were cotransfected with 2 μg pEBB-Fas plus vector or plasmids expressing indicated genes (2 μg each) and pCMV-lacZ (0.5 μg) as above. HeLa cells were transfected with 1 μg pEBB-Fas plus plasmids expressing the indicated genes (3 μg each) and pCMV-lacZ (0.5 μg); Jo2 (12.5 ng/ml) addition and X-gal staining was done as above. It was found that Fas-induced apoptosis in L929, 293, and HeLa cells can be blocked by crmA and Bcl-2-type inhibitors, but only 293 cells and L929 cells required the JNK pathway for Fas-induced apoptosis (FIG. 8A). This result is consistent with the work of Liu et. al., who reported that the JNK pathway appeared dispensable for TNF-α-induced apoptosis in HeLa cells (Liu et al., Cell 87:565–576, 1996). Kolesnick and colleagues have previously shown that TNF-α-induced apoptosis is inhibited in U937 human monoblastic leukemia cells that stably express TAM67 (Verheij et al., 1996); assayed as above, we found that these cells are also resistant to Fas-mediated apoptosis. Taken together, these observations indicate that the requirement for the JNK pathway in Fas-mediated apoptosis is cell-type specific. It should be noted that this type of dominant negative experiment gives a positive result only if the protein in question is uniquely required for a particular process. In a case where a negative result (no inhibition) is obtained, it may be that the protein in question is involved but is functionally redundant or in great excess. The continued discovery of JNK relatives makes such scenarios plausible (Gupta et al., EMBO J. 15:2760–2770, 1996).

Next, the same panel of inhibitor genes was tested on FADD and Daxx-induced apoptosis. Since full length Daxx does not induce apoptosis by itself, two alternative strategies were used: the apoptotic response of Fas plus Daxx in 293 cells (where a large fraction of the apoptotic response is Daxx-dependent, FIG. 4B) and the apoptotic response of Daxx 501-625, the smallest domain that has constitutive cell death activity in 293 cells (FIG. 6A), were examined. 293 cells were transiently transfected with Fas, Daxx, Daxx 501-625, or FADD (1 μg each) plus empty vector or plasmids expressing the indicated apoptotic inhibitor genes (3 μg each) and pCMV-lacZ (0.5 μg) as FIG. 4B. Daxx-dependent apoptosis was blocked by crmA, Bcl-2, and required the JNK pathway, which paralleled the inhibition profile of Fas in 293 cells (FIG. 8B). In contrast, FADD, which can not activate JNK, was inhibited only by crmA, but not by Bcl-2, SEK(AL), or TAM67. Similarly, Hsu et al. have shown that TRADD-mediated apoptosis is not blocked by Bcl-2 (Hsu et al. Cell 81:495–504, 1995). Consistent with the two pathway model, the residual Fas-induced death remaining after either DaxxC or FADD(80-205) treatment are qualitatively different: the apoptosis remaining after FADD(80-205) treatment is Bcl-2 sensitive but the apoptosis remaining after DaxxC treatment is not (FIG. 7A, lanes 8 and 9). These results suggest that Fas activates two distinct cell death pathways—one via FADD that is Bcl-2 insensitive and a second one via Daxx that activates JNK and is Bcl-2 sensitive.

Example 9
Defective Daxx signaling in Autoimmune Lymphoproliferative Disorder (ALPS)

ALPS is a disease characterized by early onset lymphadenopathy, lymphoproliferation, and autoantibody production leading to hemolytic anemia, thrombocytopenia and other autoimmune symptoms. Most patients harbor defects in the Fas apoptosis pathway (Fisher et al., *Cell* 81:935–946, 1995). As shown above, Daxx is a downstream signaling protein in the Fas pathway.

The role of Daxx in ALPS was evaluated by screening Fas mutations derived from ALPS patients for Daxx binding. Expression constructs for epitope-tagged wildtype and mutant (mu1 and mu2) human Fas cDNAs (Fisher et al., 1995) were cotransfected with pCI-FLAG-FADD or pRK5-FLAG-hDAXX and pRK5-crmA (Hsu et al., 1996) in 293T cells as described above. CrmA prevents the induction of apoptosis and allows the accumulation of transfected proteins. Twenty-four hours after transfection cells were lysed in IP-lysis buffer (Hsu et al., 1996). Immunoprecipitation with anti-AU1 antibodies (BAbCO, Berkeley, Calif.) and immunoblotting with anti FLAG-Daxx or anti-FLAG-FADD antibodies were performed as described above. FIG. 1A shows the results of the immunoblotting and FIG. 1B shows that Daxx, FADD and Fas mutants were equally expressed in all cell lysates.

FIG. 1A shows that the mu1 and mu2 Fas mutants have different binding properties. While the mu2 Fas mutation disrupts binding to both Daxx and FADD, the mu1 Fas mutation disrupts only Fas-DAXX binding. Therefore a selective defect in Daxx binding by Fas (such as in mu1) is sufficient to cause ALPS. The selective Daxx defect conferred by Fas mu1 us correlated with a distinct clinical disease. In the analysis of ALPS mu1 pateints, the mu1 mutation cosegregated with a high incidence of lymphomas in addition to autoimmune disease in the affected families; lymphomas are not generally observed with ALPS patients. Therefore determining the Daxx binding property of Fas mutants in ALPS has prognostic value. Dysregulation of the Daxx pathway also may be involved in other autoimmune diseases or tumorigenesis.

Example 10
ASK1 is a Downstream Target of Daxx

As demonstrated above, Daxx activates the Jun N-terminal kinase (JNK) and enhances Fas-induced apoptosis. It has now been discovered that apoptosis signal-regulating kinase 1 (ASK1; Ichijo et al., *Science* 275:90–94, 1997), an upstream kinase in the JNK pathway, is a downstream target of Daxx.

To determine if Daxx interacted with ASK1, 4.0 μg of pRK5-FLAG-hDaxx, pcDNA3, or pcDNA3-Myc-ASK1 were cotransfected with 2.0 μg of pRK5-crmA in 293T cells. Twenty-four hours after transfection cells were extracted in IP-lysis buffera and immunoprecipitated with anti-Myc mAb coupled to agarose beads (Santa Cruz Biotech, Santa Cruz, Calif.). Immunoprecipitation samples and extract aliquots were resolved by SDS-PAGE and immunoblotted by M2 anti-FLAG antibody (Kodak) as described above. As shown in FIG. 10A, epitope-tagged Daxx and ASK1 expressed in 293T cells were co-immunoprecipitated, demonstrating that Daxx and ASK1 interact in mammalian cells.

To determined if endogenous ASK1 is recruited to Fas, $1.5 \times 10^7$ L929/Fas cells were incubated in the presence or absence of 2 μg/ml anti-Fas antibody Jo2 (Pharmingen, ) for 30 minutes. Cells were washed once in ice-cold PBS and lysed in 1 ml IP-lysis buffer. Post-nuclear supernatant was immunoprecipitated with 40 μl of protein A/G-agarose (Santa Cruz) for 3 hours at 4° C. In samples without Jo2 preincubation, 2 μg/ml isotype-matched control antibody (FIG. 10B, lane 1) of Jo2 (FIG. 10B, lane 2) were added after cell lysis. Immunoprecipitates were washed 5 times with 500 μl lysis buffer, resolved by 7.5% SDS-PAGE and immunoblotted for ASK1 by an ASK1-specific antiserum. As shown in FIG. 10, lane 3, ASK1 is recruited to Fas in a ligand-dependent manner, presumably through the Fas-Daxx and Daxx-ASK1 interactions.

The interaction of ASK1 with Daxx can be used to evaluate mutations in either gene in human diseases such as autoimmune disorders. The Daxx-ASK1 complex also can be used to screen for compounds which reduce the binding of these two proteins and thereby reduce activity of the Daxx pathway. The demonstration that endogenous ASK1 can be recruited to Fas provides an assay for testing Fas and Daxx function in patients having autoimmune disease to determine if the Fas-Daxx pathway is involved.

All patents and other documents disclosed in this application are incorporated in their entirety herein by reference.

Those skilled in the art will recognize, or be able to ascertain using no more than routine experimentation, many equivalents to the specific embodiments of the invention described herein. Such equivalents are intended to be encompassed by the following claims.

A sequence listing is presented below and is followed by what is claimed:

We claim:

1. An isolated nucleic acid molecule
   (a) which hybridizes under stringent conditions to a molecule consisting of the nucleic acid sequence of SEQ ID NO:1 or SEQ ID NO:4 and which codes for a polypeptide which binds to Fas,
   (b) nucleic acid molecules that differ from the nucleic acid molecules of (a) in codon sequence due to the degeneracy of the genetic code, and
   (c) complements of (a) and (b).

2. The isolated nucleic acid molecule of claim 1, wherein the isolated nucleic acid molecule comprises nucleotides 25-2241 of SEQ ID NO:1.

3. The isolated nucleic acid molecule of claim 1, wherein the isolated nucleic acid molecule comprises nucleotides 1-2220 of SEQ ID NO:4.

4. An isolated nucleic acid molecule selected from the group consisting of (a) a unique fragment of nucleotides 25-2241 of SEQ ID NO:1 between 12 and 2215 nucleotides in length, (b) a unique fragment of nucleotides 1-2220 of SEQ ID NO:4 between 12 and 2199 nucleotides in length, (c) complements of "(a)", and (d) complements of "(b)".

5. The isolated nucleic acid molecule of claim 4, wherein the isolated nucleic acid molecule consists of at least 14 contiguous nucleotides.

6. The isolated nucleic acid molecule of claim 4, wherein the isolated nucleic acid molecule consists of at least 15 contiguous nucleotides.

7. The isolated nucleic acid molecule of claim 4, wherein the isolated nucleic acid molecule consists of at least 16 contiguous nucleotides.

8. The isolated nucleic acid molecule of claim 4, wherein the isolated nucleic acid molecule consists of at least 17 contiguous nucleotides.

9. The isolated nucleic acid molecule of claim 4, wherein the isolated nucleic acid molecule consists of at least 18 contiguous nucleotides.

10. The isolated nucleic acid molecule of claim 4, wherein the isolated nucleic acid molecule consists of at least 20 contiguous nucleotides.

11. The isolated nucleic acid molecule of claim 4, wherein the isolated nucleic acid molecule consists of at least 22 contiguous nucleotides.

12. The isolated nucleic acid molecule of claim 4, wherein the isolated nucleic acid molecule consists of between 12–32 contiguous nucleotides.

13. An expression vector comprising the isolated nucleic acid molecule of claim 1 operably linked to a promoter.

14. A host cell transformed or transfected with the expression vector of claim 13.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2358 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
    (A) NAME/KEY: Coding Sequence
    (B) LOCATION: 25...2241

(xi) SEQUENCE DESCRIPTION: SEQ ID NO:1:

```
TTTCTGAGGG GAATTTGAAC CCCC ATG GCC ACC GAT GAC AGC ATC ATT GTA            51
                          Met Ala Thr Asp Asp Ser Ile Ile Val
                          1               5

CTT GAT GAT GAC GAT GAA GAT GAA GCT GCT GCT CAA CCA GGG CCC TCC           99
Leu Asp Asp Asp Asp Glu Asp Glu Ala Ala Ala Gln Pro Gly Pro Ser
10                  15                  20                  25

AAC CTA CCC CCC AAT CCT GCC TCA ACA GGA CCT GGT CCT GGC CTG TCT          147
Asn Leu Pro Pro Asn Pro Ala Ser Thr Gly Pro Gly Pro Gly Leu Ser
                30                  35                  40

CAA CAG GCC ACT GGT CTC TCC GAG CCC CGT GTG GAT GGA GGG AGC AGT          195
Gln Gln Ala Thr Gly Leu Ser Glu Pro Arg Val Asp Gly Gly Ser Ser
            45                  50                  55

AAC TCC GGT AGT AGG AAG TGC TAC AAG TTG GAT AAT GAG AAG CTC TTT          243
Asn Ser Gly Ser Arg Lys Cys Tyr Lys Leu Asp Asn Glu Lys Leu Phe
        60                  65                  70

GAA GAG TTC CTT GAA CTG TGT AAG ACG GAG ACA TCA GAC CAC CCT GAG          291
Glu Glu Phe Leu Glu Leu Cys Lys Thr Glu Thr Ser Asp His Pro Glu
75                  80                  85

GTG GTT CCG TTC CTC CAC AAA CTG CAG CAG CGT GCC CAG TCT GTG TTT          339
Val Val Pro Phe Leu His Lys Leu Gln Gln Arg Ala Gln Ser Val Phe
90                  95                  100                 105

CTG GCC TCT GCA GAG TTC TGC AAC ATC CTC TCC AGG GTT CTG GCT CGG          387
Leu Ala Ser Ala Glu Phe Cys Asn Ile Leu Ser Arg Val Leu Ala Arg
                110                 115                 120

TCT CGG AAG CGG CCC GCT AAG ATC TAT GTG TAC ATT AAC GAG CTC TGC          435
Ser Arg Lys Arg Pro Ala Lys Ile Tyr Val Tyr Ile Asn Glu Leu Cys
            125                 130                 135

ACT GTT CTT AAA GCT CAC TCC ATC AAG AAG AAG TTG AAC TTA GCT CCT          483
Thr Val Leu Lys Ala His Ser Ile Lys Lys Lys Leu Asn Leu Ala Pro
        140                 145                 150

GCA GCC TCA ACG ACC AGT GAG GCG TCG GGC CCT AAC CCT CCC ACA GAG          531
Ala Ala Ser Thr Thr Ser Glu Ala Ser Gly Pro Asn Pro Pro Thr Glu
    155                 160                 165

CCC CCC TCT GAC CTT ACA AAC ACT GAA AAC ACT GCC TCT GAG GCC TCA          579
Pro Pro Ser Asp Leu Thr Asn Thr Glu Asn Thr Ala Ser Glu Ala Ser
170                 175                 180                 185

AGG ACT CGC GGT TCC CGG AGG CAG ATC CAG CGC CTG GAG CAG CTG CTG          627
Arg Thr Arg Gly Ser Arg Arg Gln Ile Gln Arg Leu Glu Gln Leu Leu
                190                 195                 200

GCA CTG TAT GTA GCC GAG ATT CGG CGG CTG CAG GAG AAG GAG TTG GAC          675
Ala Leu Tyr Val Ala Glu Ile Arg Arg Leu Gln Glu Lys Glu Leu Asp
            205                 210                 215

CTG TCA GAG CTG GAT GAC CCA GAC TCC TCG TAT TTG CAG GAG GCC CGC          723
Leu Ser Glu Leu Asp Asp Pro Asp Ser Ser Tyr Leu Gln Glu Ala Arg
        220                 225                 230

TTG AAG AGG AAG TTG ATC CGC CTC TTC GGG CGG TTG TGT GAG TTG AAG          771
Leu Lys Arg Lys Leu Ile Arg Leu Phe Gly Arg Leu Cys Glu Leu Lys
    235                 240                 245

GAC TGC TCT TCT CTG ACG GGG CGG GTC ATA GAG CAG CGA ATT CCG TAC          819
Asp Cys Ser Ser Leu Thr Gly Arg Val Ile Glu Gln Arg Ile Pro Tyr
250                 255                 260                 265

CGA GGC ACC CGG TAC CCA GAG GTC AAC AGG CGC ATT GAA CGG CTC ATT          867
Arg Gly Thr Arg Tyr Pro Glu Val Asn Arg Arg Ile Glu Arg Leu Ile
                270                 275                 280

AAC AAG CCG GGG CTG GAC ACC TTC CCC GAT TAT GGA GAT GTG CTG AGA          915
```

```
                Asn Lys Pro Gly Leu Asp Thr Phe Pro Asp Tyr Gly Asp Val Leu Arg
                            285                 290                 295

GCC GTG GAG AAG GCG GCG ACC CGG CAC AGC CTG GGC CTT CCC AGA CAG        963
Ala Val Glu Lys Ala Ala Thr Arg His Ser Leu Gly Leu Pro Arg Gln
            300                 305                 310

CAG CTT CAG CTC CTG GCT CAG GAT GCC TTC CGG GAC GTG GGC GTC AGG       1011
Gln Leu Gln Leu Leu Ala Gln Asp Ala Phe Arg Asp Val Gly Val Arg
            315                 320                 325

TTA CAG GAG CGG CGC CAC CTG GAT CTC ATC TAC AAC TTT GGC TGT CAC       1059
Leu Gln Glu Arg Arg His Leu Asp Leu Ile Tyr Asn Phe Gly Cys His
330                 335                 340                 345

CTC ACA GAT GAC TAT AGG CCA GGC GTT GAC CCC GCA CTG TCT GAT CCC       1107
Leu Thr Asp Asp Tyr Arg Pro Gly Val Asp Pro Ala Leu Ser Asp Pro
                350                 355                 360

ACA TTG GCT CGC CGC CTT CGG GAA AAT CGA ACC TTG GCC ATG AAC CGG       1155
Thr Leu Ala Arg Arg Leu Arg Glu Asn Arg Thr Leu Ala Met Asn Arg
                365                 370                 375

CTG GAT GAG GTC ATC TCC AAG TAT GCA ATG ATG CAA GAC AAG ACT GAG       1203
Leu Asp Glu Val Ile Ser Lys Tyr Ala Met Met Gln Asp Lys Thr Glu
            380                 385                 390

GAG GGC GAG AGA CAG AAG AGA CGA GCC CGG CTC TTA GGC ACC GCC CCC       1251
Glu Gly Glu Arg Gln Lys Arg Arg Ala Arg Leu Leu Gly Thr Ala Pro
            395                 400                 405

CAA CCT TCA GAC CCC CCC CAA GCC TCC TCG GAA TCT GGT GAG GGT CCT       1299
Gln Pro Ser Asp Pro Pro Gln Ala Ser Ser Glu Ser Gly Glu Gly Pro
410                 415                 420                 425

AGC GGA ATG GCA TCC CAG GAG TGC CCT ACT ACC TCC AAA GCT GAG ACT       1347
Ser Gly Met Ala Ser Gln Glu Cys Pro Thr Thr Ser Lys Ala Glu Thr
                430                 435                 440

GAT GAT GAC GAT GAT GAC GAT GAT GAC GAC GAC GAA GAT AAC GAG GAA       1395
Asp Asp Asp Asp Asp Asp Asp Asp Asp Asp Asp Glu Asp Asn Glu Glu
                445                 450                 455

AGT GAG GAG GAG GAG GAG GAG GAA GAG GAG GAG AAA GAG GCT ACT GAA       1443
Ser Glu Glu Glu Glu Glu Glu Glu Glu Glu Glu Lys Glu Ala Thr Glu
            460                 465                 470

GAT GAA GAT GAG GAT CTA GAA CAG TTG CAG GAA GAT CAG GGG GGT GAT       1491
Asp Glu Asp Glu Asp Leu Glu Gln Leu Gln Glu Asp Gln Gly Gly Asp
            475                 480                 485

GAA GAA GAG GAA GGA GGA GAT AAT GAA GGA AAT GAG AGT CCC ACA TCG       1539
Glu Glu Glu Glu Gly Gly Asp Asn Glu Gly Asn Glu Ser Pro Thr Ser
490                 495                 500                 505

CCT TCA GAC TTT TTC CAT AGA AGG AAT TCA GAG CCT GCA GAA GGG CTC       1587
Pro Ser Asp Phe Phe His Arg Arg Asn Ser Glu Pro Ala Glu Gly Leu
                510                 515                 520

AGG ACC CCC GAG GGG CAG CAA AAG AGA GGA CTG ACA GAG ACC CCA GCA       1635
Arg Thr Pro Glu Gly Gln Gln Lys Arg Gly Leu Thr Glu Thr Pro Ala
            525                 530                 535

TCC CCG CCA GGG GCA TCC CTG GAC CCT CCC AGC ACT GAC GCT GAG AGC       1683
Ser Pro Pro Gly Ala Ser Leu Asp Pro Pro Ser Thr Asp Ala Glu Ser
            540                 545                 550

AGT GGA GAG CAG CTC CTC GAG CCG CTC CTG GGA GAC GAG AGT CCT GTG       1731
Ser Gly Glu Gln Leu Leu Glu Pro Leu Leu Gly Asp Glu Ser Pro Val
555                 560                 565

TCC CAG CTC GCT GAG CTA GAG ATG GAA GCT TTG CCT GAG GAA AGG GAC       1779
Ser Gln Leu Ala Glu Leu Glu Met Glu Ala Leu Pro Glu Glu Arg Asp
570                 575                 580                 585

ATT TCC TCC CCC AGG AAA AAG TCG GAA GAT CCT CTC CCC ACC ATC TTG       1827
Ile Ser Ser Pro Arg Lys Lys Ser Glu Asp Ser Leu Pro Thr Ile Leu
                590                 595                 600
```

-continued

```
GAA AAT GGG GCA GCT GTG GTT ACC TCT ACA TCT GTC AAT GGG CGT GTC      1875
Glu Asn Gly Ala Ala Val Val Thr Ser Thr Ser Val Asn Gly Arg Val
            605                 610                 615

TCT TCT CAC ACT TGG AGA GAT GCC AGT CCC CCC AGC AAG AGA TTT CGG      1923
Ser Ser His Thr Trp Arg Asp Ala Ser Pro Pro Ser Lys Arg Phe Arg
            620                 625                 630

AAG GAA AAG AAG CAA CTG GGC TCT GGA CTG TTA GGA AAC AGC TAT ATA      1971
Lys Glu Lys Lys Gln Leu Gly Ser Gly Leu Leu Gly Asn Ser Tyr Ile
635                 640                 645

AAA GAA CCG ATG GCA CAG CAG GAC AGT GGG CAG AAC ACA AGT GTC CAG      2019
Lys Glu Pro Met Ala Gln Gln Asp Ser Gly Gln Asn Thr Ser Val Gln
650                 655                 660                 665

CCT ATG CCA TCC CCC CCC TTG GCC TCT GTG GCT TCT GTC GCT GAT TCC      2067
Pro Met Pro Ser Pro Pro Leu Ala Ser Val Ala Ser Val Ala Asp Ser
            670                 675                 680

TCC ACA AGG GTG GAC TCT CCC AGC CAT GAA CTG GTG ACC AGC TCT CTG      2115
Ser Thr Arg Val Asp Ser Pro Ser His Glu Leu Val Thr Ser Ser Leu
            685                 690                 695

TGC AGC CCT TCT CCA TCC CTG CTT CTC CAG ACA CCC CAG GCT CAG TCT      2163
Cys Ser Pro Ser Pro Ser Leu Leu Leu Gln Thr Pro Gln Ala Gln Ser
            700                 705                 710

CTC CGG CAG TGT ATT TAT AAG ACC AGT GTG GCC ACA CAG TGC GAC CCG      2211
Leu Arg Gln Cys Ile Tyr Lys Thr Ser Val Ala Thr Gln Cys Asp Pro
715                 720                 725

GAG GAG ATC ATC GTG CTT TCA GAC TCT GAT TAGCAGGCCC CATGCTCCCC GTG    2264
Glu Glu Ile Ile Val Leu Ser Asp Ser Asp
730                 735

CTCCCTGCAT CCAGAAGGTT TTTTGTATGG CTGTTGGAAG ATGATGGAGT AAAAGATGGA    2324

CAGAGCTCCT CCCGTTTTGA TGGTGTTTCT TTTG                                2358

(2) INFORMATION FOR SEQ ID NO:2:

(i) SEQUENCE CHARACTERISTICS:
        (A) LENGTH: 739 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ala Thr Asp Ser Ile Ile Val Leu Asp Asp Asp Glu Asp
1               5                   10                  15

Glu Ala Ala Gln Pro Gly Pro Ser Asn Leu Pro Asn Pro Ala
            20                  25                  30

Ser Thr Gly Pro Gly Pro Gly Leu Ser Gln Gln Ala Thr Gly Leu Ser
            35                  40                  45

Glu Pro Arg Val Asp Gly Gly Ser Ser Asn Ser Gly Ser Arg Lys Cys
50                  55                  60

Tyr Lys Leu Asp Asn Glu Lys Leu Phe Glu Glu Phe Leu Glu Leu Cys
65                  70                  75                  80

Lys Thr Glu Thr Ser Asp His Pro Glu Val Val Pro Phe Leu His Lys
                85                  90                  95

Leu Gln Gln Arg Ala Gln Ser Val Phe Leu Ala Ser Ala Glu Phe Cys
                100                 105                 110

Asn Ile Leu Ser Arg Val Leu Ala Arg Ser Arg Lys Arg Pro Ala Lys
                115                 120                 125
```

-continued

```
Ile Tyr Val Tyr Ile Asn Glu Leu Cys Thr Val Leu Lys Ala His Ser
    130                 135                 140
Ile Lys Lys Leu Asn Leu Ala Pro Ala Ser Thr Thr Ser Glu
145                 150                 155                 160
Ala Ser Gly Pro Asn Pro Thr Glu Pro Ser Asp Leu Thr Asn
                165                 170                 175
Thr Glu Asn Thr Ala Ser Glu Ala Ser Arg Thr Arg Gly Ser Arg Arg
                180                 185                 190
Gln Ile Gln Arg Leu Glu Gln Leu Leu Ala Leu Tyr Val Ala Glu Ile
            195                 200                 205
Arg Arg Leu Gln Glu Lys Glu Leu Asp Leu Ser Glu Leu Asp Asp Pro
    210                 215                 220
Asp Ser Ser Tyr Leu Gln Glu Ala Arg Leu Lys Arg Lys Leu Ile Arg
225                 230                 235                 240
Leu Phe Gly Arg Leu Cys Glu Leu Lys Asp Cys Ser Ser Leu Thr Gly
                245                 250                 255
Arg Val Ile Glu Gln Arg Ile Pro Tyr Arg Gly Thr Arg Tyr Pro Glu
            260                 265                 270
Val Asn Arg Arg Ile Glu Arg Leu Ile Asn Lys Pro Gly Leu Asp Thr
    275                 280                 285
Phe Pro Asp Tyr Gly Asp Val Leu Arg Ala Val Glu Lys Ala Ala Thr
290                 295                 300
Arg His Ser Leu Gly Leu Pro Arg Gln Gln Leu Gln Leu Leu Ala Gln
305                 310                 315                 320
Asp Ala Phe Arg Asp Val Gly Val Arg Leu Gln Glu Arg Arg His Leu
                325                 330                 335
Asp Leu Ile Tyr Asn Phe Gly Cys His Leu Thr Asp Tyr Arg Pro
            340                 345                 350
Gly Val Asp Pro Ala Leu Ser Asp Pro Thr Leu Ala Arg Arg Leu Arg
                355                 360                 365
Glu Asn Arg Thr Leu Ala Met Asn Arg Leu Asp Glu Val Ile Ser Lys
    370                 375                 380
Tyr Ala Met Met Gln Asp Lys Thr Glu Glu Gly Glu Arg Gln Lys Arg
385                 390                 395                 400
Arg Ala Arg Leu Leu Gly Thr Ala Pro Gln Pro Ser Asp Pro Pro Gln
                405                 410                 415
Ala Ser Ser Glu Ser Gly Glu Gly Pro Ser Gly Met Ala Ser Gln Glu
            420                 425                 430
Cys Pro Thr Thr Ser Lys Ala Glu Thr Asp Asp Asp Asp Asp Asp
    435                 440                 445
Asp Asp Asp Asp Glu Asp Asn Glu Glu Ser Glu Glu Glu Glu Glu
    450                 455                 460
Glu Glu Glu Glu Lys Glu Ala Thr Glu Asp Glu Asp Glu Asp Leu Glu
465                 470                 475                 480
Gln Leu Gln Glu Asp Gln Gly Gly Asp Glu Glu Glu Gly Gly Asp
                485                 490                 495
Asn Glu Gly Asn Glu Ser Pro Thr Ser Pro Ser Asp Phe Phe His Arg
                500                 505                 510
Arg Asn Ser Glu Pro Ala Glu Gly Leu Arg Thr Pro Glu Gly Gln Gln
            515                 520                 525
Lys Arg Gly Leu Thr Glu Thr Pro Ala Ser Pro Gly Ala Ser Leu
    530                 535                 540
Asp Pro Pro Ser Thr Asp Ala Glu Ser Ser Gly Glu Gln Leu Leu Glu
```

```
545              550              555              560
Pro Leu Leu Gly Asp Glu Ser Pro Val Ser Gln Leu Ala Glu Leu Glu
                565              570              575
Met Glu Ala Leu Pro Glu Arg Asp Ile Ser Ser Pro Arg Lys Lys
            580              585              590
Ser Glu Asp Ser Leu Pro Thr Ile Leu Glu Asn Gly Ala Ala Val Val
            595              600              605
Thr Ser Thr Ser Val Asn Gly Arg Val Ser Ser His Thr Trp Arg Asp
610              615              620
Ala Ser Pro Pro Ser Lys Arg Phe Arg Lys Glu Lys Lys Gln Leu Gly
625              630              635              640
Ser Gly Leu Leu Gly Asn Ser Tyr Ile Lys Glu Pro Met Ala Gln Gln
                645              650              655
Asp Ser Gly Gln Asn Thr Ser Val Gln Pro Met Pro Ser Pro Pro Leu
                660              665              670
Ala Ser Val Ala Ser Val Ala Asp Ser Ser Thr Arg Val Asp Ser Pro
            675              680              685
Ser His Glu Leu Val Thr Ser Ser Leu Cys Ser Pro Ser Pro Ser Leu
            690              695              700
Leu Leu Gln Thr Pro Gln Ala Gln Ser Leu Arg Gln Cys Ile Tyr Lys
705              710              715              720
Thr Ser Val Ala Thr Gln Cys Asp Pro Glu Glu Ile Ile Val Leu Ser
                725              730              735
Asp Ser Asp
```

(2) INFORMATION FOR SEQ ID NO:3:

(i) SEQUENCE CHARACTERISTICS:
        (A) LENGTH: 864 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GACAAGAGCC CCATGTCCTC ACTACAGATC TCCAATGAAA AGAACCTGGA ACCTGGCAAA      60

CAGATCAGCA GATCTTCAGG GGAGCAGCAA AACAAAGGAC GCATAGTGTC ACCATCGTTA     120

CTGTCAGAAG AACCCCTGGC CCCTCCAGC ATAGATGCTG AAAGCAATGG AGAACAGCCT     180

GAGGAGCTGA CCCTGGAGGA AGAAAGCCCT GTGTCTCAGC TCTTTGAGCT AGAGATTGAA     240

GCTTTGCCCC TGGATACCCC TTCCTCTGTG GAGACGGACA TTTCCTCTTC CAGGAAGCAA     300

TCAGAGGAGC CCTTCACCAC TGTCTTAGAG AATGGAGCAG GCATGGTCTC TTCTACTTCC     360

TTCAATGGAG GCGTCTCTCC TCACAACTGG GGAGATTCTG GTCCCCCCTG CAAAAAATCT     420

CGGAAGGAGA GAAGCAAAC AGGATCAGGG CCATTAGGAA ACAGCTATGT GGAAAGGCAA     480

AGGTCAGTGC ATGAGAAGAA TGGGAAAAAG ATATGTACCC TGCCCAGCCC ACCTTCCCCC     540

TTGGCTTCCT TGGCCCCAGT TGCTGATTCC TCCACGAGGG TGGACTCTCC CAGCCATGGC     600

CTGGTGACCA GCTCCCTCTG CATCCCTTCT CCAGCCCGGC TGTCCCAAAC CCCCCATTCA     660

CAGCCTCCTC GGCCTGGTAC TTGCAAGACA AGTGTGGCCA CACAATGCGA TCCAGAAGAG     720

ATCATCGTGC TCTCAGACTC TGATTAACTG CCTCCCCTTC TCCCTGCCTC CAGAATGTTC     780

TGGGATAACA TTTGGAGGAA GGTGGGAAGC AGATGACTGA GGAAGGGATG GACTAAGCTA     840

ATCCCCTTTT GGTGGTGTTT CTTT                                            864
```

(2) INFORMATION FOR SEQ ID NO:4:

(i) SEQUENCE CHARACTERISTICS:
        (A) LENGTH: 2340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: Coding Sequence
        (B) LOCATION: 1...2220

(xi) SEQUENCE DESCRIPTION: SEQ ID NO:4:

```
ATG GCC ACC GCT AAC AGC ATC ATC GTG CTG GAT GAT GAT GAC GAA GAT      48
Met Ala Thr Ala Asn Ser Ile Ile Val Leu Asp Asp Asp Asp Glu Asp
 1               5                  10                  15

GAA GCA GCT GCT CAG CCA GGG CCC TCC CAC CCA CTC CCC AAT GCG GCC      96
Glu Ala Ala Ala Gln Pro Gly Pro Ser His Pro Leu Pro Asn Ala Ala
             20                  25                  30

TCA CCT GGG GCA GAA GCC CCT AGC TCC TCT GAG CCT CAT GGG GCC AGA     144
Ser Pro Gly Ala Glu Ala Pro Ser Ser Ser Glu Pro His Gly Ala Arg
         35                  40                  45

GGA AGC AGT AGT TCG GGC GGC AAG AAA TGC TAC AAG CTG GAG AAT GAG     192
Gly Ser Ser Ser Ser Gly Gly Lys Lys Cys Tyr Lys Leu Glu Asn Glu
     50                  55                  60

AAG CTG TTC GAA GAG TTC CTT GAA CTT TGT AAG ATG CAG ACA GCA GAC     240
Lys Leu Phe Glu Glu Phe Leu Glu Leu Cys Lys Met Gln Thr Ala Asp
 65                  70                  75                  80

CAC CCT GAG GTG GTC CCA TTC CTC TAT AAC CGG CAG CAA CGT GCC CAC     288
His Pro Glu Val Val Pro Phe Leu Tyr Asn Arg Gln Gln Arg Ala His
                 85                  90                  95

TCT CTG TTT TTG GCC TCG GCG GAG TTC TGC AAC ATC CTC TCT AGG GTC     336
Ser Leu Phe Leu Ala Ser Ala Glu Phe Cys Asn Ile Leu Ser Arg Val
            100                 105                 110

CTG TCT CGG GCC CGG AGC CGG CCA GCC AAG CTC TAT GTC TAC ATC AAT     384
Leu Ser Arg Ala Arg Ser Arg Pro Ala Lys Leu Tyr Val Tyr Ile Asn
        115                 120                 125

GAG CTC TGC ACT GTT CTC AAG GCC CAC TCA GCC AAA AAG AAG CTG AAC     432
Glu Leu Cys Thr Val Leu Lys Ala His Ser Ala Lys Lys Lys Leu Asn
    130                 135                 140

TTG GCC CCT GCC GCC ACC ACC TCC AAT GAG CCC TCT GGG AAT AAC CCT     480
Leu Ala Pro Ala Ala Thr Thr Ser Asn Glu Pro Ser Gly Asn Asn Pro
145                 150                 155                 160

CCC ACA CAC CTC TCC TTG GAC CCC ACA AAT GCT GAA AAC ACT GCC TCT     528
Pro Thr His Leu Ser Leu Asp Pro Thr Asn Ala Glu Asn Thr Ala Ser
                165                 170                 175

CAG TCT CCA AGG ACC CGT GGT TCC CGG CGG CAG ATC CAG CGT TTG GAG     576
Gln Ser Pro Arg Thr Arg Gly Ser Arg Arg Gln Ile Gln Arg Leu Glu
            180                 185                 190

CAG CTG CTG GCG CTC TAT GTG GCA GAG ATC CGG CGG CTG CAG GAA AAG     624
Gln Leu Leu Ala Leu Tyr Val Ala Glu Ile Arg Arg Leu Gln Glu Lys
        195                 200                 205

GAG TTG GAT CTC TCA GAA TTG GAT GAC CCA GAC TCC GCA TAC CTG CAG     672
Glu Leu Asp Leu Ser Glu Leu Asp Asp Pro Asp Ser Ala Tyr Leu Gln
    210                 215                 220

GAG GCA CGG TTG AAG CGT AAG CTG ATC CGC CTC TTT GGG CGA CTA TGT     720
Glu Ala Arg Leu Lys Arg Lys Leu Ile Arg Leu Phe Gly Arg Leu Cys
```

```
Glu Ala Arg Leu Lys Arg Lys Leu Ile Arg Leu Phe Gly Arg Leu Cys
225                 230                 235                 240

GAG CTG AAA GAC TGC TCT TCA CTG ACC GGC CGT GTC ATA GAG CAG CGC            768
Glu Leu Lys Asp Cys Ser Ser Leu Thr Gly Arg Val Ile Glu Gln Arg
                245                 250                 255

ATC CCC TAC CGT GGC ACC CGC TAC CCA GAG GTT AAC AGG CGC ATT GAG            816
Ile Pro Tyr Arg Gly Thr Arg Tyr Pro Glu Val Asn Arg Arg Ile Glu
            260                 265                 270

CGG CTC ATC AAC AAG CCA GGG CCT GAT ACC TTC CCT GAC TAT GGG GAT            864
Arg Leu Ile Asn Lys Pro Gly Pro Asp Thr Phe Pro Asp Tyr Gly Asp
            275                 280                 285

GTG CTT CGG GCT GTA GAG AAG GCA GCT GCC CGA CAC AGC CTT GGC CTC            912
Val Leu Arg Ala Val Glu Lys Ala Ala Ala Arg His Ser Leu Gly Leu
        290                 295                 300

CCC CGA CAG CAG CTC CAG CTC ATG GCT CAG GAT GCC TTC CGA GAT GTG            960
Pro Arg Gln Gln Leu Gln Leu Met Ala Gln Asp Ala Phe Arg Asp Val
305                 310                 315                 320

GGC ATC AGG TTA CAG GAG CGA CGT CAC CTC GAT CTC ATC TAC AAC TTT           1008
Gly Ile Arg Leu Gln Glu Arg Arg His Leu Asp Leu Ile Tyr Asn Phe
                325                 330                 335

GGC TGC CAC CTC ACA GAT GAC TAT AGG CCA GGC GTT GAC CCT GCA CTA           1056
Gly Cys His Leu Thr Asp Asp Tyr Arg Pro Gly Val Asp Pro Ala Leu
                340                 345                 350

TCA GAT CCT GTG TTG GCC CGG CGC CTT CGG GAA AAC CGG AGT TTG GCC           1104
Ser Asp Pro Val Leu Ala Arg Arg Leu Arg Glu Asn Arg Ser Leu Ala
            355                 360                 365

ATG AGT CGG CTG GAT GAG GTC ATC TCC AAA TAC GCA ATG TTG CAA GAC           1152
Met Ser Arg Leu Asp Glu Val Ile Ser Lys Tyr Ala Met Leu Gln Asp
        370                 375                 380

AAA AGT GAG GAG GGC GAG AGA AAA AAG AGA AGA GCT CGG CTC CAA GGC           1200
Lys Ser Glu Glu Gly Glu Arg Lys Lys Arg Arg Ala Arg Leu Gln Gly
385                 390                 395                 400

ACC TCT TCC CAC TCT GCA GAC ACC CCC GAA GCC TCC TTG GAT TCT GGT           1248
Thr Ser Ser His Ser Ala Asp Thr Pro Glu Ala Ser Leu Asp Ser Gly
                405                 410                 415

GAG GGC CCT AGT GGA ATG GCA TCC CAG GGG TGC CCT TCT GCC TCC AGA           1296
Glu Gly Pro Ser Gly Met Ala Ser Gln Gly Cys Pro Ser Ala Ser Arg
                420                 425                 430

GCT GAG ACA GAT GAC GAA GAC GAT GAG GAG AGT GAT GAG GAA GAG GAG           1344
Ala Glu Thr Asp Asp Glu Asp Asp Glu Glu Ser Asp Glu Glu Glu Glu
            435                 440                 445

GAG GAG GAG GAA GAA GAA GAG GAG GAG GCC ACA GAT TCT GAA GAG GAG           1392
Glu Glu Glu Glu Glu Glu Glu Glu Glu Ala Thr Asp Ser Glu Glu Glu
        450                 455                 460

GAG GAT CTG GAA CAG ATG CAG GAG GGT CAG GAG GAT GAT GAA GAG GAG           1440
Glu Asp Leu Glu Gln Met Gln Glu Gly Gln Glu Asp Asp Glu Glu Glu
465                 470                 475                 480

GAC GAA GAG GAA GAA GCA GCA GCA GGT AAA GAT GGA GAC AAG AGC CCC           1488
Asp Glu Glu Glu Glu Ala Ala Ala Gly Lys Asp Gly Asp Lys Ser Pro
                485                 490                 495

ATG TCC TCA CTA CAG ATC TCC AAT GAA AAG AAC CTG GAA CCT GGC AAA           1536
Met Ser Ser Leu Gln Ile Ser Asn Glu Lys Asn Leu Glu Pro Gly Lys
                500                 505                 510

CAG ATC AGC AGA TCT TCA GGG GAG CAG CAA AAC AAA GGA CGC ATA GTG           1584
Gln Ile Ser Arg Ser Ser Gly Glu Gln Gln Asn Lys Gly Arg Ile Val
            515                 520                 525

TCA CCA TCG TTA CTG TCA GAA GAA CCC CTG GCC CCC TCC AGC ATA GAT           1632
Ser Pro Ser Leu Leu Ser Glu Glu Pro Leu Ala Pro Ser Ser Ile Asp
        530                 535                 540
```

```
GCT GAA AGC AAT GGA GAA CAG CCT GAG GAG CTG ACC CTG GAG GAA GAA      1680
Ala Glu Ser Asn Gly Glu Gln Pro Glu Glu Leu Thr Leu Glu Glu Glu
545                 550                 555                 560

AGC CCT GTG TCT CAG CTC TTT GAG CTA GAG ATT GAA GCT TTG CCC CTG      1728
Ser Pro Val Ser Gln Leu Phe Glu Leu Glu Ile Glu Ala Leu Pro Leu
                565                 570                 575

GAT ACC CCT TCC TCT GTG GAG ACG GAC ATT TCC TCT TCC AGG AAG CAA      1776
Asp Thr Pro Ser Ser Val Glu Thr Asp Ile Ser Ser Ser Arg Lys Gln
            580                 585                 590

TCA GAG GAG CCC TTC ACC ACT GTC TTA GAG AAT GGA GCA GGC ATG GTC      1824
Ser Glu Glu Pro Phe Thr Thr Val Leu Glu Asn Gly Ala Gly Met Val
        595                 600                 605

TCT TCT ACT TCC TTC AAT GGA GGC GTC TCT CCT CAC AAC TGG GGA GAT      1872
Ser Ser Thr Ser Phe Asn Gly Gly Val Ser Pro His Asn Trp Gly Asp
    610                 615                 620

TCT GGT CCC CCC TGC AAA AAA TCT CGG AAG GAG AAG AAG CAA ACA GGA      1920
Ser Gly Pro Pro Cys Lys Lys Ser Arg Lys Glu Lys Lys Gln Thr Gly
625                 630                 635                 640

TCA GGG CCA TTA GGA AAC AGC TAT GTG GAA AGG CAA AGG TCA GTG CAT      1968
Ser Gly Pro Leu Gly Asn Ser Tyr Val Glu Arg Gln Arg Ser Val His
                645                 650                 655

GAG AAG AAT GGG AAA AAG ATA TGT ACC CTG CCC AGC CCA CCT TCC CCC      2016
Glu Lys Asn Gly Lys Lys Ile Cys Thr Leu Pro Ser Pro Pro Ser Pro
            660                 665                 670

TTG GCT TCC TTG GCC CCA GTT GCT GAT TCC TCC ACG AGG GTG GAC TCT      2064
Leu Ala Ser Leu Ala Pro Val Ala Asp Ser Ser Thr Arg Val Asp Ser
        675                 680                 685

CCC AGC CAT GGC CTG GTG ACC AGC TCC CTC TGC ATC CCT TCT CCA GCC      2112
Pro Ser His Gly Leu Val Thr Ser Ser Leu Cys Ile Pro Ser Pro Ala
    690                 695                 700

CGG CTG TCC CAA ACC CCC CAT TCA CAG CCT CCT CGG CCT GGT ACT TGC      2160
Arg Leu Ser Gln Thr Pro His Ser Gln Pro Pro Arg Pro Gly Thr Cys
705                 710                 715                 720

AAG ACA AGT GTG GCC ACA CAA TGC GAT CCA GAA GAG ATC ATC GTG CTC      2208
Lys Thr Ser Val Ala Thr Gln Cys Asp Pro Glu Glu Ile Ile Val Leu
                725                 730                 735

TCA GAC TCT GAT TAACTGCCTC CCCTTCTCCC TGCCTCCAGA ATGTTCTGGG ATAAC    2265
Ser Asp Ser Asp
            740

ATTTGGAGGA AGGTGGGAAG CAGATGACTG AGGAAGGGAT GGACTAAGCT AATCCCCTTT    2325

TGGTGGTGTT TCTTT                                                     2340

(2) INFORMATION FOR SEQ ID NO:5:

(i) SEQUENCE CHARACTERISTICS:
        (A) LENGTH: 740 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

Met Ala Thr Ala Asn Ser Ile Ile Val Leu Asp Asp Asp Glu Asp
 1               5                  10                  15

Glu Ala Ala Ala Gln Pro Gly Pro Ser His Pro Leu Pro Asn Ala Ala
                20                  25                  30

Ser Pro Gly Ala Glu Ala Pro Ser Ser Glu Pro His Gly Ala Arg
            35                  40                  45
```

-continued

Gly Ser Ser Ser Ser Gly Gly Lys Lys Cys Tyr Lys Leu Glu Asn Glu
    50                  55                  60

Lys Leu Phe Glu Glu Phe Leu Glu Leu Cys Lys Met Gln Thr Ala Asp
65                  70                  75                  80

His Pro Glu Val Val Pro Phe Leu Tyr Asn Arg Gln Gln Arg Ala His
                85                  90                  95

Ser Leu Phe Leu Ala Ser Ala Glu Phe Cys Asn Ile Leu Ser Arg Val
            100                 105                 110

Leu Ser Arg Ala Arg Ser Arg Pro Ala Lys Leu Tyr Val Tyr Ile Asn
        115                 120                 125

Glu Leu Cys Thr Val Leu Lys Ala His Ser Ala Lys Lys Lys Leu Asn
    130                 135                 140

Leu Ala Pro Ala Ala Thr Thr Ser Asn Glu Pro Ser Gly Asn Asn Pro
145                 150                 155                 160

Pro Thr His Leu Ser Leu Asp Pro Thr Asn Ala Glu Asn Thr Ala Ser
                165                 170                 175

Gln Ser Pro Arg Thr Arg Gly Ser Arg Arg Gln Ile Gln Arg Leu Glu
            180                 185                 190

Gln Leu Leu Ala Leu Tyr Val Ala Glu Ile Arg Arg Leu Gln Glu Lys
        195                 200                 205

Glu Leu Asp Leu Ser Glu Leu Asp Asp Pro Asp Ser Ala Tyr Leu Gln
    210                 215                 220

Glu Ala Arg Leu Lys Arg Lys Leu Ile Arg Leu Phe Gly Arg Leu Cys
225                 230                 235                 240

Glu Leu Lys Asp Cys Ser Ser Leu Thr Gly Arg Val Ile Glu Gln Arg
                245                 250                 255

Ile Pro Tyr Arg Gly Thr Arg Tyr Pro Glu Val Asn Arg Arg Ile Glu
            260                 265                 270

Arg Leu Ile Asn Lys Pro Gly Pro Asp Thr Phe Pro Asp Tyr Gly Asp
        275                 280                 285

Val Leu Arg Ala Val Glu Lys Ala Ala Ala Arg His Ser Leu Gly Leu
    290                 295                 300

Pro Arg Gln Gln Leu Gln Leu Met Ala Gln Asp Ala Phe Arg Asp Val
305                 310                 315                 320

Gly Ile Arg Leu Gln Glu Arg Arg His Leu Asp Leu Ile Tyr Asn Phe
                325                 330                 335

Gly Cys His Leu Thr Asp Asp Tyr Arg Pro Gly Val Asp Pro Ala Leu
            340                 345                 350

Ser Asp Pro Val Leu Ala Arg Arg Leu Arg Glu Asn Arg Ser Leu Ala
        355                 360                 365

Met Ser Arg Leu Asp Glu Val Ile Ser Lys Tyr Ala Met Leu Gln Asp
    370                 375                 380

Lys Ser Glu Glu Gly Glu Arg Lys Lys Arg Arg Ala Arg Leu Gln Gly
385                 390                 395                 400

Thr Ser Ser His Ser Ala Asp Thr Pro Glu Ala Ser Leu Asp Ser Gly
                405                 410                 415

Glu Gly Pro Ser Gly Met Ala Ser Gln Gly Cys Pro Ser Ala Ser Arg
            420                 425                 430

Ala Glu Thr Asp Asp Glu Asp Asp Glu Glu Ser Asp Glu Glu Glu Glu
        435                 440                 445

Glu Glu Glu Glu Glu Glu Glu Glu Glu Ala Thr Asp Ser Glu Glu Glu
    450                 455                 460

-continued

```
Glu Asp Leu Glu Gln Met Gln Glu Gly Gln Glu Asp Asp Glu Glu Glu
465                 470                 475                 480

Asp Glu Glu Glu Glu Ala Ala Ala Gly Lys Asp Gly Asp Lys Ser Pro
                485                 490                 495

Met Ser Ser Leu Gln Ile Ser Asn Glu Lys Asn Leu Glu Pro Gly Lys
            500                 505                 510

Gln Ile Ser Arg Ser Ser Gly Glu Gln Gln Asn Lys Gly Arg Ile Val
        515                 520                 525

Ser Pro Ser Leu Leu Ser Glu Glu Pro Leu Ala Pro Ser Ser Ile Asp
    530                 535                 540

Ala Glu Ser Asn Gly Glu Gln Pro Glu Glu Leu Thr Leu Glu Glu Glu
545                 550                 555                 560

Ser Pro Val Ser Gln Leu Phe Glu Leu Glu Ile Glu Ala Leu Pro Leu
                565                 570                 575

Asp Thr Pro Ser Ser Val Glu Thr Asp Ile Ser Ser Ser Arg Lys Gln
            580                 585                 590

Ser Glu Glu Pro Phe Thr Thr Val Leu Glu Asn Gly Ala Gly Met Val
        595                 600                 605

Ser Ser Thr Ser Phe Asn Gly Gly Val Ser Pro His Asn Trp Gly Asp
    610                 615                 620

Ser Gly Pro Pro Cys Lys Lys Ser Arg Lys Glu Lys Lys Gln Thr Gly
625                 630                 635                 640

Ser Gly Pro Leu Gly Asn Ser Tyr Val Glu Arg Gln Arg Ser Val His
                645                 650                 655

Glu Lys Asn Gly Lys Lys Ile Cys Thr Leu Pro Ser Pro Pro Ser Pro
            660                 665                 670

Leu Ala Ser Leu Ala Pro Val Ala Asp Ser Ser Thr Arg Val Asp Ser
        675                 680                 685

Pro Ser His Gly Leu Val Thr Ser Ser Leu Cys Ile Pro Ser Pro Ala
    690                 695                 700

Arg Leu Ser Gln Thr Pro His Ser Gln Pro Pro Arg Pro Gly Thr Cys
705                 710                 715                 720

Lys Thr Ser Val Ala Thr Gln Cys Asp Pro Glu Glu Ile Ile Val Leu
                725                 730                 735

Ser Asp Ser Asp
            740
```